United States Patent
Chen et al.

(10) Patent No.: US 9,886,745 B2
(45) Date of Patent: Feb. 6, 2018

(54) MULTI-SHOT SCAN PROTOCOLS FOR HIGH-RESOLUTION MRI INCORPORATING MULTIPLEXED SENSITIVITY-ENCODING (MUSE)

(71) Applicant: Duke University, Durham, NC (US)

(72) Inventors: Nan-Kuei Chen, Cary, NC (US); Allen W. Song, Chapel Hill, NC (US)

(73) Assignee: Duke University, Durham, NC (US)

( * ) Notice: Subject to any disclaimer, the term of this patent is extended or adjusted under 35 U.S.C. 154(b) by 433 days.

(21) Appl. No.: 14/409,355

(22) PCT Filed: Jun. 27, 2013

(86) PCT No.: PCT/US2013/048252
§ 371 (c)(1),
(2) Date: Dec. 18, 2014

(87) PCT Pub. No.: WO2014/004870
PCT Pub. Date: Jan. 3, 2014

(65) Prior Publication Data
US 2015/0154741 A1   Jun. 4, 2015

Related U.S. Application Data

(60) Provisional application No. 61/665,494, filed on Jun. 28, 2012.

(51) Int. Cl.
*G06K 9/00* (2006.01)
*G06T 5/00* (2006.01)
(Continued)

(52) U.S. Cl.
CPC ............ *G06T 5/002* (2013.01); *G01R 33/543* (2013.01); *G01R 33/5615* (2013.01);
(Continued)

(58) Field of Classification Search
None
See application file for complete search history.

(56) References Cited

U.S. PATENT DOCUMENTS 6,842,000 B2 *  1/2005  Norris ............. G01R 33/56509
                                                      324/309
7,170,289 B2 *  1/2007  Kumai ................. A61B 5/7257
                                                      324/307

(Continued)

FOREIGN PATENT DOCUMENTS

WO   WO 2011/106649 A1   9/2011
WO   WO 2012/047771 A2   4/2012

OTHER PUBLICATIONS

Office Action corresponding to U.S. Appl. No. 13/928,757 (6 pages) (dated Sep. 22, 2016).
(Continued)

*Primary Examiner* — Nancy Bitar
(74) *Attorney, Agent, or Firm* — Myers Bigel, P.A.

(57) ABSTRACT

Multi-shot DWI with multiplexed sensitivity-encoding (MUSE) inherently corrects nonlinear shot-to-shot phase variations without requiring the use of navigator echoes. The multi-shot DWI can use interleaved echo-planar imaging or other scan protocols. This new technique should prove highly valuable for mapping brain structures and connectivities at high spatial resolution for neuroscience studies.

42 Claims, 21 Drawing Sheets
(3 of 21 Drawing Sheet(s) Filed in Color)

(51) Int. Cl.
| | |
|---|---|
| G01R 33/54 | (2006.01) |
| G01R 33/563 | (2006.01) |
| G01R 33/565 | (2006.01) |
| G06T 7/00 | (2017.01) |
| H04N 7/18 | (2006.01) |
| G01R 33/561 | (2006.01) |
| G06T 7/20 | (2017.01) |
| A61B 5/055 | (2006.01) |

(52) U.S. Cl.
CPC . *G01R 33/56341* (2013.01); *G01R 33/56509* (2013.01); *G06T 5/001* (2013.01); *G06T 7/0012* (2013.01); *H04N 7/18* (2013.01); *A61B 5/055* (2013.01); *G01R 33/5611* (2013.01); *G01R 33/5616* (2013.01); *G06T 7/20* (2013.01)

(56) References Cited

U.S. PATENT DOCUMENTS

| | | | | |
|---|---|---|---|---|
| 7,205,763 | B2 | 4/2007 | Porter | |
| 7,259,557 | B2* | 8/2007 | Hinks | G01R 33/56554 324/307 |
| 7,375,519 | B2 | 5/2008 | Yuyal | |
| 7,411,394 | B2* | 8/2008 | Huang | G01R 33/56341 324/307 |
| 7,420,370 | B2* | 9/2008 | Hinks | G01R 33/56341 324/307 |
| 7,696,753 | B2* | 4/2010 | Nozaki | G01R 33/5616 324/307 |
| 8,482,280 | B2* | 7/2013 | Huo | G01R 33/4824 324/307 |
| 8,483,457 | B2 | 7/2013 | Hinks et al. | |
| 8,731,267 | B2* | 5/2014 | Nakanishi | A61B 6/032 382/131 |
| 8,760,163 | B2 | 6/2014 | Frost et al. | |
| 9,047,695 | B2* | 6/2015 | Tseng | G06T 11/003 |
| 9,097,778 | B2* | 8/2015 | Bito | G01R 33/485 |
| 9,329,252 | B2* | 5/2016 | Bammer | G01R 33/56 |
| 2001/0008376 | A1 | 7/2001 | Mock | |
| 2008/0157767 | A1* | 7/2008 | Bammer | G01R 33/4824 324/312 |
| 2009/0001984 | A1* | 1/2009 | Hwang | G01R 33/5611 324/307 |

OTHER PUBLICATIONS

Extended European Search Report for related European Application No. EP13809232.5, dated May 30, 2016, 11 pages.
Mani et al., Accelerating Non-Cartesian Sense for Large Coil Arrays: Application to Motion Compensation in Multishot DWI, 2012 IEEE International Symposium on Biomedical Imaging (ISBI), pp. 406-409.
Uecker et al., Inverse Reconstruction Method for Segmented Multishot Diffusion-Weighted MRI with Multiple Coils, Magnetic Resonance in Medicine, 2000, pp. 1342-1348, vol. 62.
Anderson et al. "Analysis and correction of motion artifacts in diffusion weighted imaging", *Magn. Reson. Med.*, 32: 379-387, 1994.
Andersson et al. "A model-based method for retrospective correction of geometric distortions in diffusion-weighted epi", Neuroimage, 16 (1), 177-99, May 2002.
Atkinson et al. "Nonlinear phase correction of navigated multi-coil diffusion images", Magn Reson Med. 56 (50, 1135-9, Nov. 2006.
Atkinson et al. "Sampling and Reconstruction Effects Due to Motion in Diffusion-Weighted Interleaved Echo Planar Imaging", *Magn Reson Med*, 44:101-109, 2000.
Bammer et al. "Augmented generalized SENSE reconstruction to correct for rigid body motion", Magn Reson Med, 57 (1), 90-102, Jan. 2007.
Bammer et al. "Diffusion-weighted imaging with navigated interleaved echo-planar imaging and a conventional gradient system", Radiology, 211 (3), 799-806, Jun. 1999.
Butts et al. "Diffusion-Weighted Interleaved Echo-Planar Imaging with a Pair of Orthogonal Navigator Echoes", MRM 35:763-770, 1996.
Butts et al. "Interleaved echo planar imaging on a standard MRI system", *Magn Reson Med*, 31(1):67-72, Jan. 1994.
Bydder et al. "SMASH navigators", Magn Reson Med, 49 (3), 493-500, Mar. 2003.
Chen et al. "A robust multi-shot scan strategy for high-resolution diffusion weighted MRI enabled by multiplexed sensitivity-encoding (MUSE)", *NeuroImage*, 72, 41-47, 2013.
Chen et al. "Two-Dimensional Phase Cycled Reconstruction for Inherent Correction of Echo-Planar Imaging Nyquist Artifacts", *Magn Reson Med*, 66:1057-1066, 2011.
Farzaneh et al. "Analysis of t2 limitations and off-resonance effects on spatial resolution and artifacts in echo-planar imaging", Magn Reson Med. 14 (1), 123-39, Apr. 1990.
Feinberg et al. "Multiplexed echo planar imaging for sub-second whole brain FMRI and fast diffusion imaging", PLoS One, 5 (12), e15710, 2010.
Griswold et al. "Generalized Autocalibrating Partially Parallel Acquisitions (GRAPPA)", *Magn Reson Med*, 47:1202-1210, 2002.
Holdsworth et al. "Diffusion tensor imaging (dti) with retrospective motion correction for large-scale pediatric imaging", J. Magn Reson Imaging, 36 (4), 961-71, Oct. 2012.
Jeong et al. "High-Resolution Human Diffusion Tensor Imaging Using 2-D Navigated Multishot SENSE EPI at 7 T", *Magn Reson Med*, 69:793-802, 2013.
Jezzard et al. "Characterization of and correction for eddy current artifacts in echo planar diffusion imaging", Magn Reson Med. 39, (5), 801-812, May 1998.
Le Bihan et al. "Separation of diffusion and perfusion in intravoxel incoherent motion MR imaging", Radiology, 168 (2), 497-505, 1998.
Li et al. "X-PROP: a fast and robust diffusion-weighted propeller technique", Magn Reson Med 66 (2), 341-7, Aug. 2011.
Liu et al. "Self-Navigated Interleaved Spiral (SNAILS): Application to High-Resolution Diffusion Tensor Imaging", *Magn. Reson. Med.*, 52:1388-1396, 2004.
Miller et al. "Nonlinear Phase Correction for Navigated Diffusion Imaging", *Magn Reson Med*, 50:343-353, 2003.
Mohammadi et al. "Correcting eddy current and motion effects by affine whole-brain registrations: evaluation of three-dimensional distortions and comparison with slicewise correction", Magn Reson Med, 64 (4), 1047-56, Oct. 2010.
Moseley et al. "Diffusion-weighted MR imaging of anisotropic water diffusion in cat central nervous system", Radiology, 176 (2), 439-45, Aug. 1990.
Pipe et al. "Multishot Diffusion-Weighted FSE Using PROPELLER MRI", *Magn Reson Med*, 47:42-52, 2002.
Porter et al. "High resolution diffusion-weighted imaging using readout-segmented echo-planar imaging, parallel imaging and a two-dimensional navigator-based reacquisition", Magn Reson Med., 62 (2), 468-75, Aug. 2009.
Pruessmann et al. "SENSE: sensitivity encoding for fast MRI", *Magn. Reson. Med.*, Nov. 1999, 42(5):952-962.
Robson et al. "Diffusion-Weighted Multiple Shot Echo Planar Imaging of Humans without Navigation", MRM, 38:82-88, 1997.
Rudin et al. Nonlinear total variation based noise removal algorithms, Physica D, 6 (1-4), 259-268, 1992.
Skare et al. "Propeller EPI in the other direction", Magn Reson Med. 55 (6), 1298-307, Jun. 2006.
Sodickson et al. "Simultaneous Acquisition of Spatial Harmonics (SMASH): Fast Imaging with Radiofrequency Coil Arrays", *MRM* 38:591-603, 1977.
Truong et al. "Inherent Correction of Motion-Induced Phase Errors in Multishot Spiral Diffusion-Weighted Imaging", *Magn Reson Med*, 68:1255-1261, 2012.
Turner et al. "Echo-planar imaging of duffusion and perfusion", Magn Reson Med. 19 (2), 247-53, Jun. 1991.

(56) References Cited

OTHER PUBLICATIONS

Wang et al. "PROPELLER EPI: an MRI technique suitable for diffusion tensor imaging at high field strength with reduced geometric distortions", Magn Reson Med. 54 (5), 1232-40, Nov. 2005.
International Search Report and Written Opinion Corresponding to International Application No. PCT/US2013/048252; dated Sep. 26, 2013; 10 Pages.
International Preliminary Report on Patentability Corresponding to International Application No. PCT/US2013/048252; dated Jan. 8, 2015; 7 Pages.
Basser et al. "MR Diffusion *Tensor* Spectroscopy and Imaging" *Biophysical Journal* 66:259-267 (1994).

\* cited by examiner

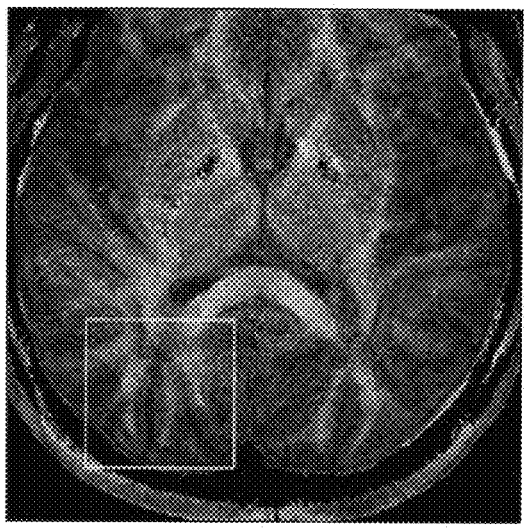 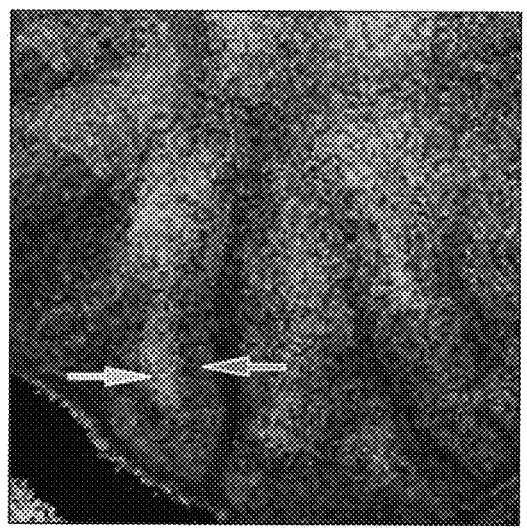
FIG. 4A　　　　　　　　　　　FIG. 4B
 
FIG. 4C　　　　　　　　　　　FIG. 4D

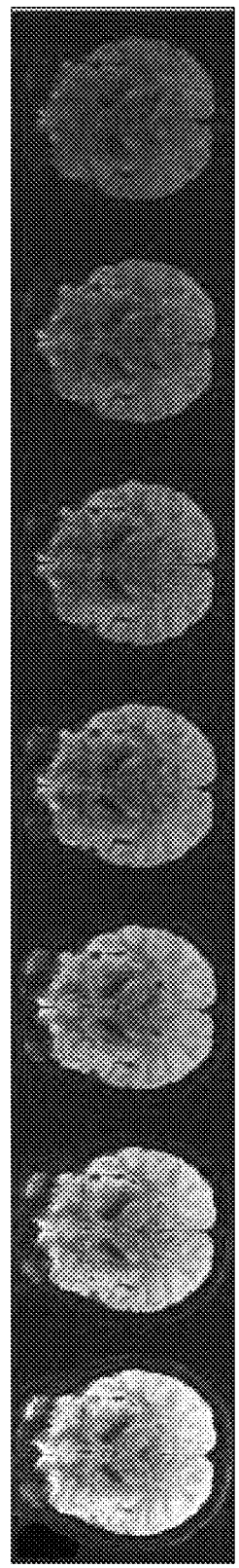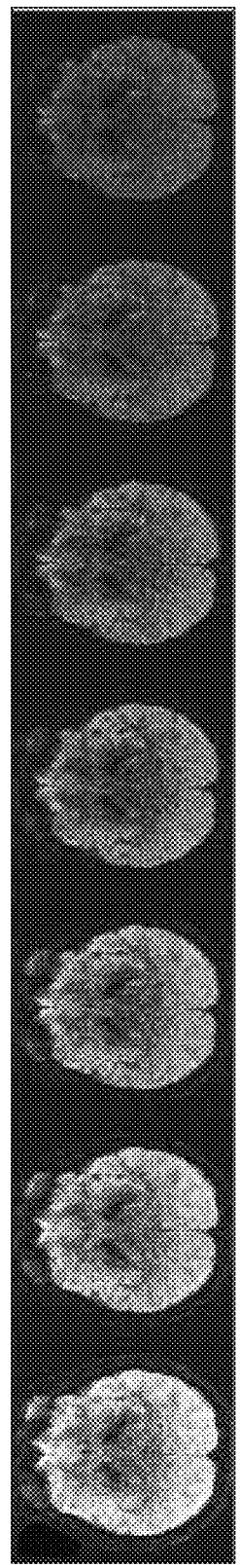
FIG. 5A
FIG. 5B

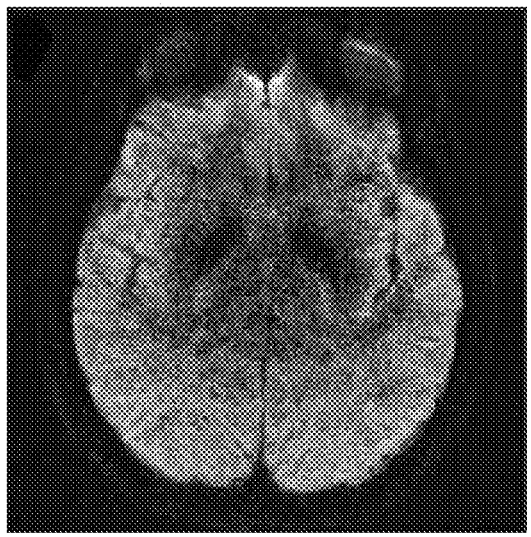
FIG. 5C  FIG. 5D
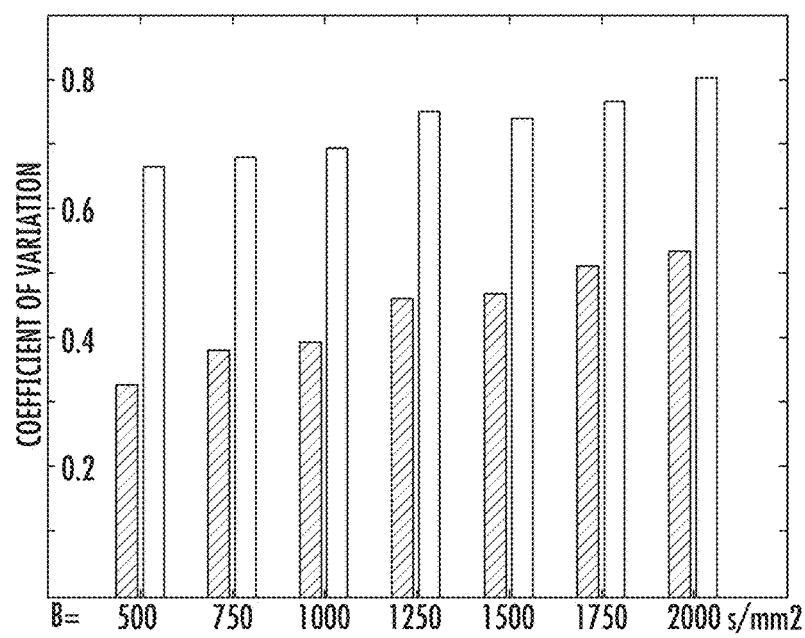
FIG. 5E

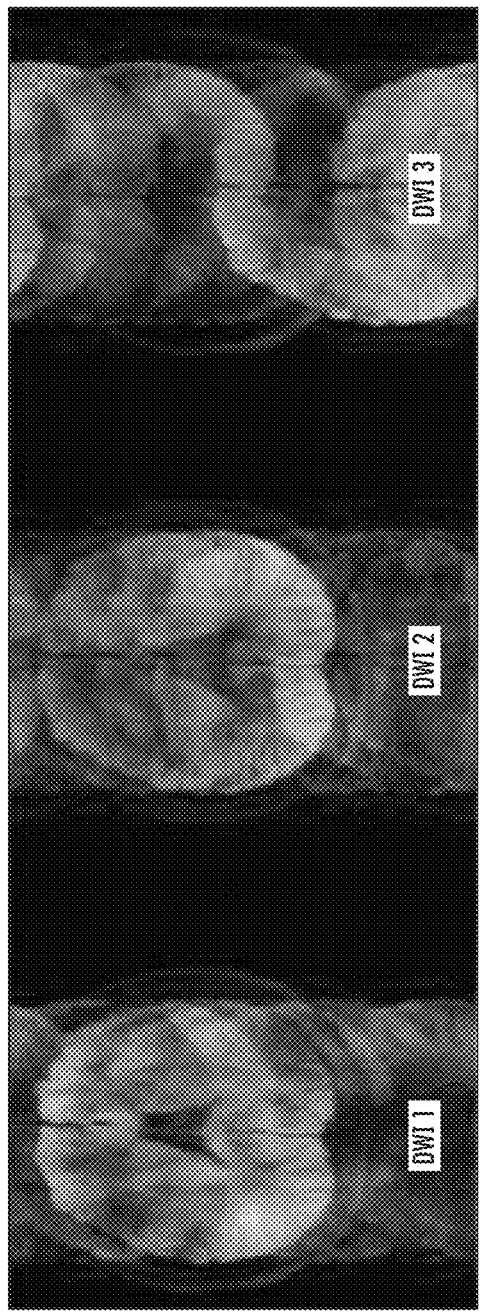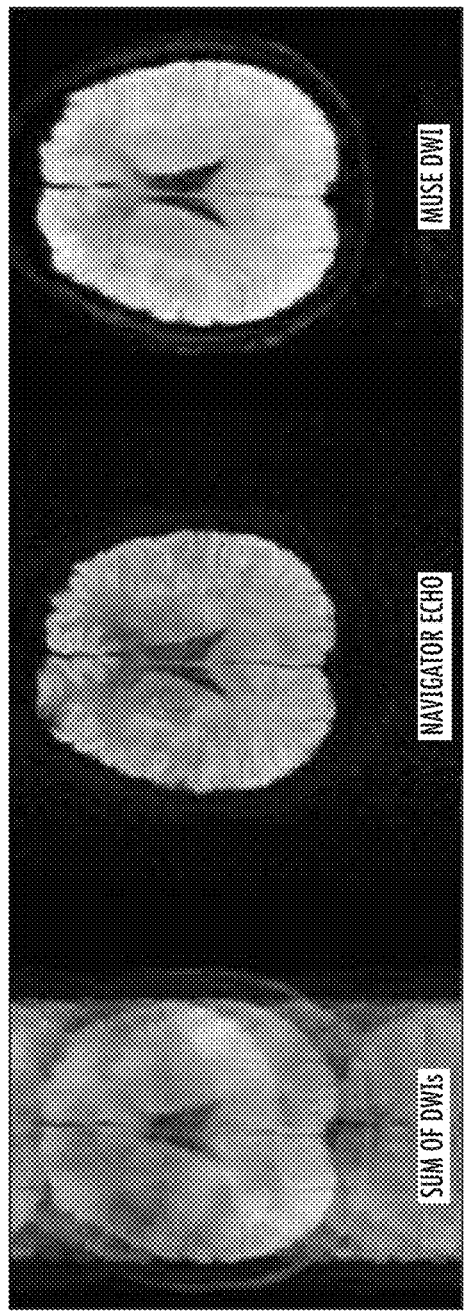

MULTI-SHOT SCAN PROTOCOLS FOR HIGH-RESOLUTION MRI INCORPORATING MULTIPLEXED SENSITIVITY-ENCODING (MUSE)

RELATED APPLICATIONS

This application claims the benefit of and priority to U.S. Provisional Application Ser. No. 61/665,494, filed Jun. 28, 2012, the contents of which are hereby incorporated by reference as if recited in full herein.

STATEMENT OF FEDERAL SUPPORT

This invention was made with government support under Grant Nos. R01 NS 074045, R01 EB 009483, and R01 NS 075017 awarded by the National Institutes of Health. The United States government has certain rights in this invention.

BACKGROUND

The emergence of diffusion weighted imaging (DWI) and diffusion tensor imaging (DTI) provides a means via water diffusion to investigate the white matter integrity in the human brain and its impact on neuronal functions. Quantitative mapping of tissue diffusion properties, such as the apparent diffusion coefficient (ADC) and fractional anisotropy (FA) derived from DWI and DTI scans, is sensitive to the pathological changes in various diseases, and is therefore clinically valuable. Diffusion-weighted magnetic resonance imaging (DWI) techniques, including diffusion tensor imaging (DTI), are now among the most powerful tools for assessing the neuronal microstructures in vivo [1,2,3]. To date, DWI data have been commonly acquired with single-shot pulse sequences, such as single-shot echo-planar imaging (EPI) [4], to avoid significant artifacts resulting from amplified motion-induced phase errors [5]. However, single-shot DWI is often limited in spatial resolution [6], making it difficult to measure detailed diffusion properties in fine structures where high spatial resolution is required [7].

Significant efforts have been invested to address the resolution limitation in DWI. Advances in parallel imaging techniques have enabled higher spatial resolution and fidelity using under-sampled k-space data at a chosen acceleration factor [8]. However, when using a lower acceleration factor (e.g., 2), parallel DWI is still limited by geometric distortions and the less-than-ideal point-spread-function. On the other hand, when using a higher acceleration factor, the noise is undesirably amplified in reconstructed parallel MR images. To uproot these limitations, multi-shot techniques such as interleaved EPI, interleaved spiral imaging, PROPELLER, and fast spin-echo pulse sequences with embedded or inherent low-resolution navigator echoes have been developed to address the amplified shot-to-shot motion-induced phase variations, and produce adequate high resolution DWI data [9,10,11,12,13,14,15,16,17,18]. However, navigator-echo based correction can fail if the motions differ between the navigation and the actual DWI data acquisition. Alternative phase correction schemes without using navigator echoes have also been proposed. For example, it has been shown that the linear terms of motion-induced phase errors may be estimated from interleaved DWI with an iterative, and often time-consuming, computation algorithm in post-processing without navigation [19]. However, this iterative computation framework may not be effective in correcting nonlinear phase errors resulting from local motions in multi-shot DWI data. It has been shown that linear and nonlinear phase variations in multi-shot DWI can be inherently estimated from the embedded low-resolution signals of variable-density spiral imaging [20,21,22]. A potential concern with the variable-density spiral imaging methods is that the imaging throughput may be compromised when a high-resolution navigator echo is desired.

SUMMARY OF EMBODIMENTS OF THE INVENTION

Embodiments of the present invention address the aforementioned technical challenges with a novel technique using multiplexed sensitivity-encoding (MUSE) to achieve high spatial resolution, high SNR, high spatial fidelity, and minimal motion-induced phase errors—all inherently without the need for (but optionally using) navigator echoes.

The MUSE method can employ a conventional SENSE technique [23] to estimate the motion-induced phase variations among multiple EPI segments and then can jointly calculate the magnitude signals of aliased voxels (due to intra-scan motion) simultaneously from all segments of interleaved EPI. In comparison to the conventional SENSE procedure, the MUSE method has a greatly improved matrix inversion conditioning and thus can produce DWI or non-DWI images at higher SNR. As compared with existing navigator-based interleaved DWI methods, the MUSE protocol technique for interleaved DWI allows interleaved DWI without requiring any pulse sequence modification.

Embodiments of the invention are directed to an MRI image data signal post-processing method for generating high-resolution DWI images from multi-shot interleaved MRI pulse sequences, without relying on external navigator echoes. The methods include: (a) programmatically estimating motion induced phase variations and position changes among multiple segments of acquired DWI image data inherently using parallel image reconstruction; (b) programmatically incorporating (i) shot-to-shot phase and position variations from the estimated motion induced phase variations and position changes and (ii) defined coil sensitivity profile data into a mathematical model that can jointly calculate magnitude-value source density signals that overlap in acquired uncorrected interleaved DWI image data to generate corrected DWI image data; and (c) programmatically generating high-resolution DWI images based on the corrected data to thereby generate images free from motion-induced aliasing artifacts.

The estimating of motion induced phase variations and position changes can be carried out by using one segment of the multiple segments as a reference segment of phase and position and calculating differences in signals associated with phase and position between the reference segment and other segments of the acquired DWI image data.

The multi-shot MRI pulse sequences can be multi-shot interleaved MRI pulse sequences associated with one or more of: (i) interleaved echo-planar imaging (EPI); (ii) interleaved fast spin-echo (FSE) imaging; or (iii) interleaved spiral imaging.

The multi-shot interleaved MRI pulse sequences can be associated with interleaved echo-planar imaging (EPI), which generates EPI segments as the multiple segments, or interleaved fast spin-echo (FSE) imaging, which generates FSE segments as the multiple segments.

The estimating of motion induced phase and position variations inherently from the acquired data can be carried out by: (i) reconstructing images corresponding to different EPI or FSE segments by applying the parallel reconstruction to each individual EPI or FSE segment; and (ii) mathematically quantifying phase and position changes among multiple images generated by the reconstruction; then (iii) spatially smoothing a shot-to-shot phase variation map derived from the mathematic quantification to produce phase information of high signal-to-noise ratio.

The method may include deriving coil sensitivity profile data for the parallel image reconstruction from a baseline T2-weighted EPI of a respective acquired DWI image data set.

The phase variations between different EPI or FSE segments can be calculated by comparing phase values of complex-value images corresponding to different segments.

Rotational and translational motions between different EPI or FSE segments can be computed from k-space data corresponding to different segments.

The phase information can be spatially smoothed using a spatial smoothing protocol.

The spatial smoothing protocol can include a total variation algorithm that preserves sharp edge information of the phase variation map.

DWI signals of the acquired image data from overlapping voxels can be calculated by jointly performing parallel image reconstruction of all EPI or FSE segments, with matrix inversion simultaneously applied to all EPI or FSE segments, assuming that magnitude-value signals are consistent across multiple segments in absence of large-scale intra-scan motion across segments. Phase variations across multiple EPI or FSE segments can be calculated based on the estimated phase variations and position changes.

Magnitude-value signals can be considered consistent across multiple EPI or FSE segments, even in the presence of large-scale intrascan motion across segments, using a transformation matrix that reflects rotational and translational motion that is mathematically incorporated into a joint parallel image reconstruction from all EPI or FSE segments.

The high resolution DWI images can be brain images illustrating brain structures based on properties of proton diffusivity.

The method can include generating fractional anisotropy (FA) maps of the brain using the high resolution DWI images.

Other embodiments are directed to methods for generating high-resolution DWI and DTI images from multi-shot interleaved MRI pulse sequences that include external navigator echoes. The methods can include: (a) programmatically estimating motion induced phase variations and position changes among multiple EPI or FSE segments from navigator echoes embedded in the interleaved MRI pulse sequences; (b) programmatically incorporating (i) shot-to-shot phase and position variations and (ii) known coil sensitivity data into a mathematical model that jointly calculates proton source density magnitude signals that overlap in uncorrected interleaved DWI data to generate corrected DWI data; and (c) generating high-resolution DWI and DTI images based on the corrected DWI data to thereby generate images free from aliasing artifacts.

The navigator echoes can be acquired using either low resolution single-shot sequences or high resolution parallel single-shot sequences.

The low resolution single-shot sequences, where used, can be single-shot echo planar imaging (EPI) sequences.

The high resolution parallel single-shot sequences can be parallel single-shot EPI with an acceleration factor of 2 or 4.

The multi-shot interleaved MRI pulse sequences can be associated with interleaved echo-planar imaging (EPI), which generates EPI segments as the multiple segments, or interleaved fast spin-echo (FSE) imaging, which generates FSE segments as the multiple segments.

The estimating of motion induced phase and position variations from the acquired data can be carried out by: (i) reconstructing images corresponding to different EPI or FSE segments by applying the parallel reconstruction to each individual EPI or FSE segment; and (ii) mathematically quantifying phase and position changes among multiple images generated by the reconstruction; then (iii) spatially smoothing a shot-to-shot phase variation map derived from the mathematic quantification to produce phase information of high signal-to-noise ratio.

The method can include deriving coil sensitivity profile data for the parallel image reconstruction from a baseline T2-weighted EPI of a respective acquired DWI image data set.

The phase variations between different EPI or FSE segments can be calculated by comparing phase values of complex-value images corresponding to different segments.

Rotational and translational motions between different EPI or FSE segments can be computed from k-space data corresponding to different segments.

The phase information can be spatially smoothed using a spatial smoothing protocol.

The spatial smoothing protocol can include a total variation algorithm that preserves sharp edge information of the phase variation map or any other spatial smoothing procedure.

DWI signals from overlapping voxels of the image data can be calculated by jointly performing parallel image reconstruction of all EPI or FSE segments, with matrix inversion applied simultaneously to all EPI or FSE segments, assuming that magnitude-value signals are consistent across multiple segments in absence of large-scale intra-scan motion across segments. Phase variations across multiple EPI or FSE segments can be calculated based on the estimated phase variations and position changes.

Magnitude-value signals can be considered consistent across multiple EPI or FSE segments, even with large-scale intrascan motion across segments, using a transformation matrix that reflects rotational and translational motion that is mathematically incorporated into a joint parallel image reconstruction from all EPI or FSE segments.

Still other embodiments are directed to methods for generating high-resolution fMRI images or other types of non-DWI images from multi-shot interleaved MRI pulse sequences, without relying on external navigator echoes. The methods include: (a) programmatically estimating motion induced phase variations and position changes among multiple echo planar imaging (EPI) or spiral segments inherently from acquired image data using parallel image reconstruction; (b) programmatically incorporating (i) shot-to-shot phase and position variations from the estimated motion induced phase variations and position changes and (ii) calculated or known coil sensitivity data into a mathematical model that jointly calculates proton source density signals that overlap in uncorrected interleaved fMRI data or non-DWI data to generate corrected interleaved image data; and (c) generating high-resolution fMRI images or other non-DWI images using the corrected interleaved image data to thereby generate images without motion-induced aliasing artifacts.

The multi-shot interleaved MRI pulse sequences can be associated with interleaved echo-planar imaging (EPI) which generates EPI segments as the multiple segments or interleaved spiral imaging which generates spiral segments as the multiple segments.

The estimating of motion induced phase and position variations inherently from the acquired data can be carried out by: (i) reconstructing images corresponding to different EPI or spiral segments by applying the parallel reconstruction to each individual EPI or spiral segment; and (ii) mathematically quantifying phase and position changes among multiple images generated by the reconstruction; then (iii) spatially smoothing a shot-to-shot phase variation map derived from the mathematic quantification to produce phase information of high signal-to-noise ratio.

The phase variations between different EPI or spiral segments can be calculated by comparing phase values of complex-value images corresponding to different segments.

Rotational and translational motions between different EPI or spiral segments can be computed from k-space data corresponding to different segments.

Phase information can be spatially smoothed using a spatial smoothing protocol that preserves sharp edge information of the phase variation map.

The spatial smoothing protocol can include a total variation algorithm that preserves sharp edge information of the phase variation map.

The images can be fMRI images with fMRI signals from overlapping voxels which are calculated by jointly performing parallel image reconstruction of all EPI or spiral segments, with matrix inversion simultaneously applied to all EPI or spiral segments, assuming that magnitude-value signals are consistent across multiple segments in absence of large-scale intra-scan motion across segments. Phase variations across multiple EPI or spiral segments can be calculated based on the estimated phase variations and position changes.

Magnitude-value signals can be considered consistent across multiple EPI or spiral segments, even with large-scale intrascan motion across segments, using a transformation matrix that reflects rotational and translational motion that is mathematically incorporated into a joint parallel image reconstruction from all EPI or spiral segments.

Still other embodiments are directed to methods for generating high-resolution fMRI images or other types of images using non-DWI data from multi-shot interleaved MRI pulse sequences that include external navigator echoes. The methods include: (a) programmatically estimating motion induced phase variations and position changes among multiple echo planar imaging (EPI) or spiral segments from navigator echoes embedded in the interleaved MRI pulse sequences; (b) incorporating i) shot-to-shot phase and position variations derived from the programmatic estimations and ii) calculated or known coil sensitivity data into a mathematical model that jointly calculates proton source density signals that overlap in the uncorrected interleaved fMRI or other types of non-DWI image data to generate corrected image data; and (c) generating high-resolution fMRI images or other non-DWI images using the corrected image data.

The multi-shot interleaved MRI pulse sequences can be associated with interleaved echo-planar imaging (EPI) which generates EPI segments as the multiple segments or interleaved spiral imaging which generates spiral segments as the multiple segments.

The estimating of motion induced phase and position variations inherently from the acquired data can include: (i) reconstructing images corresponding to different EPI or spiral segments by applying the parallel reconstruction to each individual EPI or spiral segment; and (ii) mathematically quantifying phase and position changes among multiple images generated by the reconstruction; then (iii) spatially smoothing a shot-to-shot phase variation map derived from the mathematic quantification to produce phase information of high signal-to-noise ratio.

The phase variations between different segments can be calculated by comparing phase values of complex-value images corresponding to different segments.

Rotational and translational motions between different segments can be computed from k-space data corresponding to different segments.

The phase information can be spatially smoothed using a spatial smoothing protocol that preserves sharp edge information of the phase variation map.

The phase smoothing protocol can include a total variation algorithm.

Image data signals from overlapping voxels can be calculated by jointly performing parallel image reconstruction of all segments, with matrix inversion simultaneously applied to all segments, assuming that magnitude-value signals are consistent across multiple segments in the absence of large-scale intra-scan motion across segments. Phase variations across multiple segments can be calculated based on the estimated phase variations and position changes.

Magnitude-value signals can be considered consistent across multiple segments, even in the presence of large-scale intrascan motion across segments, using a transformation matrix that reflects rotational and translational motion that is mathematically incorporated into a joint parallel image reconstruction from all segments.

Some embodiments are directed to an image processing circuit configured to electronically carry out any of the methods described above and/or herein.

Some embodiments are directed to an MR image processing system that includes at least one processor configured to carry out any of the methods described and/or claimed herein.

Yet other embodiments are directed to a data processing system with non-transitory computer readable storage medium having computer readable program code embodied in the medium. The computer-readable program code includes computer readable program code configured to carry out any of the methods described and/or claimed herein.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 illustrates MRI images.

of 15-direction are susceptible to motion-induced phase errors.

FIG. 2 illustrates MRI images.

which provides good anatomic resolvability.

FIG. 4A is a FA map of high in-plane resolution $$\left(\text{voxel size: } 0.3 \times 0.3 \times 8 \, mm^3; b = 500 \frac{\sec}{mm^2}\right).$$

FIG. 4B is an enlarged view of FA values for voxels inside the white box of (4A). FIG. 4C is an image with the contour of the indicated green and red voxels in FIG. 4B overlaid onto the mean DWI image. FIG. 4D is an image with the contour of the indicated green and red voxels in FIG. 4B overlaid onto the baseline T2-weighted EPI.

FIG. 5A illustrates images of MUSE-generated DWI corresponding to different b factors $$\left(\text{from 500 to 2000} \frac{\sec}{mm^2} \text{ in a 250} \frac{\sec}{mm^2} \text{step}\right).$$

FIG. 5B illustrates images of SENSE-generated images of the corresponding b factors $$\left(\text{from 500 to 2000} \frac{\sec}{mm^2}\right).$$

FIG. 5C is an image with the magnitude average of all 7 MUSE-generated DWI from FIG. 5A. FIG. 5D is an image with the magnitude average of all 7 SENSE-generated DWI from FIG. 5B. FIG. 5E is a graph of the coefficient of variation measured from white-matter ROIs of MUSE-DWI (black bars) and SENSE-DWI (white bars) corresponding to different B factors (also referred to in the lower case as "b" factors).

FIG. 8 shows MRI images: The top row of FIG. 8, FIGS. 8A, 8B and 8C, shows three raw DWI images (with diffusion sensitizing gradients applied along the left-right, anterior-posterior, and superior-inferior directions respectively) obtained with 8-shot EPI. Significantly aliasing artifacts are visible in uncorrected DWI data. The bottom row of FIG. 8, FIGS. 8D, 8E and 8F, shows the magnitude summation of three raw DWI images (left, FIG. 8D), one of the embedded high-resolution navigator echoes (middle, FIG. 8E, acquired with parallel EPI with an acceleration factor of 4), and the MUSE reconstruction of 8-shot DWI data using the phase information derived from 4× parallel navigator echoes (right, FIG. 8F).

DETAILED DESCRIPTION

Figure 1A:
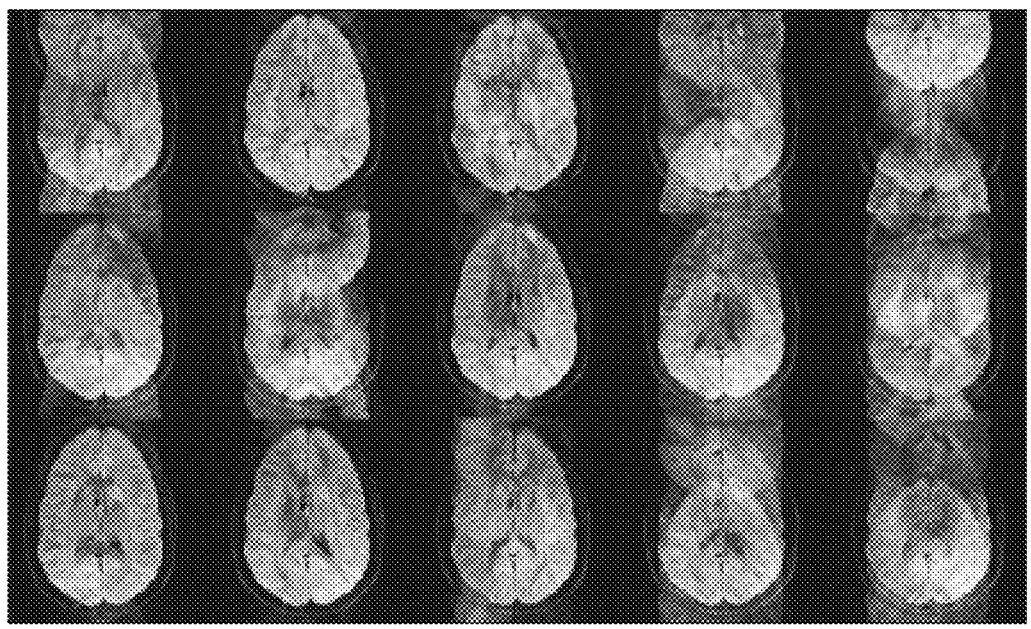
FIG. 1A: Four-shot interleaved DTI data $$\left(b = 500 \frac{\sec}{mm^2}\right)$$

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above about 0.5 T, typically above 1.0 T, and more typically between about 1.5 T and 10 T. Embodiments of the invention may be particularly suitable for 1.5 T and 3.0 T systems, or higher field systems such as future contemplated systems at 4.0 T, 5.0 T, 6.0 T, 7 T, 8 T, 9 T and the like.

The methods and systems can also be applied to animal MRI data acquired from animal MRI scanners.

The term "patient" refers to humans and animals.

The term "automatically" means that the operation can be substantially, and typically entirely, carried out without manual input, and is typically programmatically directed and/or carried out. The term "electronically" with respect to connections includes both wireless and wired connections between components.

The term "clinician" means physician, radiologist, physicist, or other medical personnel desiring to review medical data of a patient. The term "workstation" refers to a display and/or computer associated with a clinician.

The term "protocol" refers to an automated electronic algorithm and/or computer program with mathematical computations with defined rules for data interrogation, analysis and/or reconstruction that manipulates MRI image data.

The term "SENSE" refers to a sensitivy encoding protocol described by Pruessmann et al. Sense: sensitivity encoding for fast mri. Magn Reson Med 42(5), 952-62 (1999), the contents of which are hereby incorporated by reference as if recited in full herein.

The term "high resolution" means that the achieved spatial-resolution is higher than that achieved with conventional single-shot EPI pulse sequences. For example, a sub-millimeter spatial resolution which is an increase in resolution of 2× or more over conventional single shot EPI (e.g., 0.5 mm×0.5 mm), while the in-plane resolution achieved with conventional single-shot EPI is about 2 mm×2 mm).

The term "high-quality" with respect to image quality refers to a low aliasing artifact level-measured by a ghost-to-signal ratio. MR images can be considered aliasing free if the ghost-to-signal ratio (GSR) is less than 10%. The GSR of MUSE images can typically be between about 2% and about 8%. See, e.g., Chen et al., A robust multi-shot scan strategy for high-resolution diffusion weighted MRI enabled by multiplexed sensitivity-encoding (MUSE), NeuroImage 72 (2013), pp. 41-47, the contents of which are hereby incorporated by reference as if recited in full herein. Stated differently, in some embodiments, the GSR in MRI data obtained with a MUSE reconstruction can be at least three times lower than that in uncorrected interleaved DWI images.

The term "high SNR" refers to the signal-to-noise ratio, which for brain applications can be measured from the gray- and white-matter areas of brain MRI reconstructed with a MUSE procedure, is at least twice higher than in from images produced with the conventional parallel image reconstruction procedures such as SENSE. The acceptable SNR value varies with the clinical questions. For example, to detect a high-contrast visible lesion in MRI, it can be satisfactory to choose a faster protocol with a lower SNR value. In FIG. 5, the 7 images (of different b values) have different SNRs but may all be useful for different clinical questions. Thus, the term "high SNR" can be defined in relative terms instead of an absolute value of SNR threshold. For example, in FIG. 5a all have higher SNR than FIG. 5b (with different reconstruction procedures), even though the absolute SNR values corresponding to different b-values are different.

The term "interleaved EPI" is well known in the field. See, e.g., Butts K, Riederer S J, Ehman R L, Thompson R M, Jack C R. Interleaved echo planar imaging on a standard MRI system. Magn Reson Med. 1994 January; 31(1):67-72.

The term "multi-shot interleaved MRI pulse sequences" refers to MRI pulse sequences associated with interleaved echo-planar imaging (EPI), interleaved fast spin-echo (FSE) imaging, interleaved spiral imaging, and other MRI pulse sequences that acquire multiple echo trains (e.g., multiple ky lines) after a single RF pulse excitation.

The term "inherently" means that the information (e.g., motion-induced phase errors) is derived directly from the actual DWI, fMRI or other (raw) MRI image data themselves without using external signals such as navigator echoes to adjust/correct image data to reduce or eliminate motion-induced aliasing artifacts.

The term "post-processing" with respect to the claimed methods means that the method is carried out after original MRI raw data in k-space of a respective subject is obtained.

The term "large-scale intrascan motion" refers to significant patient movement, e.g., by about 1 voxel or greater than about 1 voxel during an MRI scan which generates aliasing artifacts in uncorrected interleaved EPI based DWI, fMRI or other image data.

The term "archived" refers to electronically stored patient image data that can be accessed and reconstructed into patient images/visualizations/renderings. The diagnostic task of a clinician such as a radiologist can vary patient to patient and, accordingly so can the desired renderings or views of the medical images of the patient. In some visualization systems, a physician uses an interactive workstation that has a data retrieval interface that obtains the medical data for medical image renderings from electronic volume data sets to generate desired medical representations. Image visualizations using multi-dimensional MRI image data can be carried out using any suitable system such as, for example, PACS (Picture Archiving and Communication System). PACS is a system that receives images from the imaging modalities, stores the data in archives, and distributes the data to radiologists and clinicians for viewing.

The term "reconstruction" is used broadly to refer to original or post-image data acquisition and storage and subsequent construction of image slices or images of an image data set.

It is also noted, for clarity, that while certain of the figures are described as "color" or "color-coded", to comply with filing rules, black and white copies or grey scale versions of these images may be used in support of the application.

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Generally stated, embodiments of the invention are designed to reduce, if not eliminate, the quantitative inaccuracy in MRI data acquired with the current diffusion-weighted imaging (DWI) and diffusion tensor imaging (DTI) protocols to thereby provide aliasing artifact-free MRI images.

DWI data obtained with an interleaved EPI pulse sequence are highly susceptible to aliasing artifacts as the result of amplified shot-to-shot motion-induced phase variations in the presence of strong diffusion weighting gradients. Here, without loss of generality for multi-shot acquisitions, a simplified procedure for reconstructing aliasing-free images from DWI data obtained with a 2-shot interleaved EPI sequence using a three-channel coil is described by way of example. This procedure can be readily adapted to more interleaves and larger coil arrays, as shown in experimental results. Aliased images obtained from the first and second segments of 2-shot interleaved EPI are represented by Equations 1 and 2, respectively, where $u_j$ are aliased signals detected by the j-th coil (j=1,2,3) from the first EPI segment; $v_j$ are aliased signals detected by the j-th coil (j=1,2,3) from the second EPI segment; $S_j$ are the coil sensitivity profiles for the j-th coil; and p and q are un-aliased full-FOV images that are planned for reconstruction.

$$u_j(x, y) = S_j(x, y)p(x, y) + S_j\left(x, y + \frac{FOV_y}{2}\right)p\left(x, y + \frac{FOV_y}{2}\right) \quad (1)$$

$$v_j(x, y) = S_j(x, y)q(x, y) - S_j\left(x, y + \frac{FOV_y}{2}\right)q\left(x, y + \frac{FOV_y}{2}\right) \quad (2)$$

Note that the sign before the $$S_j\left(x, y + \frac{FOV_y}{2}\right)$$

term differs between Equations 1 and 2, because of the relative k-space trajectory shift between two EPI segments. With known coil sensitivity profiles, unaliased full-FOV images can be estimated from the acquired aliased signals using parallel MRI reconstruction. For example, the full-FOV image p can be calculated from the first EPI segment using the SENSE technique [23], where the two unknowns $$\left(\text{i.e., } p(x, y) \text{ and } p\left(x, y + \frac{FOV_y}{2}\right)\right)$$

are determined from the three measured signals (i.e., $u_j(x,y)$ with j=1,2,3). Similarly, the full-FOV image q can be calculated from the second EPI segment with SENSE. The full-FOV images p and q differ mainly by the motion-induced phase inconsistencies between the two shots, as shown in Equations 3 and 4, where the non-negative real number D represents the magnitude signal (i.e., the proton-density weighted by diffusion contrast) that is expected to be consistent across multiple EPI segments; $\Theta$ and $\varphi$ are the motion-induced phase errors that differ between the two shots; and c represents the background phase value that is independent of motion. The full-FOV images estimated by the SENSE method ($p_s$ and $q_s$) can be represented by Equations 5 and 6, where $n_p$ and $n_q$ are the SENSE-produced noises that are usually significant when the number of unknowns (i.e., 2 in this example) is not much smaller than the number of equations (i.e., 3 in this example).

$$p(x,y) = D(x,y)e^{i\Theta(x,y)+c(x,y)} \quad (3)$$

$$q(x,y) = D(x,y)e^{i\varphi(x,y)+c(x,y)} \quad (4)$$

$$p_s(x,y) = p(x,y) + n_p(x,y) \quad (5)$$

$$q_s(x,y) = q(x,y) + n_q(x,y) \quad (6)$$

Even though the full-FOV images estimated by the SENSE method are susceptible to undesirable noise amplification, the shot-to-shot phase inconsistencies, which are expected to be spatially smooth, can be reliably estimated with Equations 7 and 8, where TV represents the denoising operation based on total variation [32].

$$e^{i\Theta(x,y)+c(x,y)} = \frac{TV(p_s(x, y))}{|TV(p_s(x, y))|} \quad (7)$$

$$e^{i\varphi(x,y)+c(x,y)} = \frac{TV(q_s(c, y))}{|TV(q_s(x, y))|} \quad (8)$$

At this point, Equations 1 and 2 can be reformatted to Equations 9 and 10.

$$u_j(x, y) = \left[S_j(x, y)\frac{TV(p_s(x, y))}{|TV(p_s(x, y))|}\right]D(x, y) + \left[S_j\left(x, y + \frac{FOV_y}{2}\right)\right. \tag{9}$$

$$\left.\frac{TV\left(p_s\left(x, y + \frac{FOV_y}{2}\right)\right)}{\left|TV\left(p_s\left(x, y + \frac{FOV_y}{2}\right)\right)\right|}\right]D\left(x, y + \frac{FOV_y}{2}\right)$$

$$v_j(x, y) = \left[S_j(x, y)\frac{TV(q_s(x, y))}{|TV(q_s(x, y))|}\right]D(x, y) - \tag{10}$$

$$S_j\left(x, y + \frac{FOV_y}{2}\right)\frac{TV\left(q_s\left(x, y + \frac{FOV_y}{2}\right)\right)}{\left|TV\left(q_s\left(x, y + \frac{FOV_y}{2}\right)\right)\right|}\right]D\left(x, y + \frac{FOV_y}{2}\right)$$

It can be seen that Equations 9 and 10 have two common unknowns $$\left(\text{i.e., } D(x, y) \text{ and } D\left(x, y + \frac{FOV_y}{2}\right)\right),$$

and thus can be solved jointly when the information on motion-induced phase errors $$\left(\text{e.g., } \frac{TV(p_S(x, y))}{|TV(p_S(x, y))|}\right)$$

is incorporated. The above described procedure, termed multiplexed sensitivity encoding (MUSE), has a significantly improved matrix inversion condition (with 2 unknowns and 6 equations in this example) as compared with the conventional SENSE procedure (with 2 unknowns and 3 equations in this example). Even though the MUSE procedure is described primarily herein with 2-shot EPI as an example, the MUSE framework can be directly extended to interleaved EPI with a larger number of segments. It should be noted that the multiplexed sensitivity encoding method can be a pure post-processing procedure, without requiring hardware or pulse sequence modification, and is different from the recently developed multiplexed EPI pulse sequence [24].

A series of experiments were conducted on 3 Tesla MRI systems (GEHC HD and MR750, Waukesha, Wis.) to evaluate the developed MUSE method, as described below.

To evaluate the performance of the developed technique, DTI images (0.86×0.86×4 mm³) were obtained from 6 healthy volunteers using an 8-channel receiver coil. DTI images (with one baseline acquisition, and 15 diffusion weighting directions at a b factor of either $$500 \frac{\sec}{mm^2} \text{ or } 1000 \frac{\sec}{mm^2}\right)$$

were acquired using a 4-shot interleaved EPI pulse sequence with a twice-refocused spin-echo scheme to minimize the eddy current induced geometric distortions [31]. Scan parameters included: number of partial-Fourier over-sampling ky lines 12, in-plane acquisition matrix size 256×140 (i.e., 256×256 after partial-Fourier reconstruction for a 4-shot scan), FOV 22×22 cm², axial-plane slice thickness 4 mm, TR 5 sec, and TE 59.3 msec.

Referring to FIG. 9, the acquired image data can be processed with the following steps. First, the recently developed phase-cycled reconstruction procedure [30] can be used to measure the 2D phase errors resulting from odd-even echo inconsistencies in the baseline (i.e. T2-weighted) image, and the measured information can then be used to suppress the Nyquist artifacts in both baseline and diffusion-weighted images (blocks 10, 15, 20, 30, 35). Second, the coil-sensitivity profiles can be estimated from the baseline T2-weighted images (blocks 40, 50). Third, using the conventional SENSE reconstruction procedure, full FOV images (e.g., four full-FOV images) can be reconstructed from (e.g., four) DWI segments (block 36), and the shot-to-shot phase variations can be calculated (e.g., using Equation 7)(block 38), where the total variation algorithm can be used to smooth the complex images and phase-unwrapping is not needed (block 37). Fifth, the smoothed phase maps (step 4, block 60) and the coil sensitivity profiles (step 2, block 50) can be used to reconstruct aliasing-free DWI images from the Nyquist-corrected DWI data, using the MUSE algorithm (blocks 70, 90).

It is noted that the total variation algorithm is an example of a suitable smoothing protocol and other smoothing protocols can be used, such as ones based on averaging information from neighboring voxels.

Quantitative measures of proton diffusion values, such as the fractional anisotropy (FA) values, can be calculated from the aliasing-free DTI or fMRI data.

In order to illustrate the noise reduction and SNR improvement as an advantage by the MUSE procedure, another set of aliasing-free DTI data was generated by summing the phase-corrected maps derived from four EPI segments with the conventional SENSE procedure (i.e., in step 3 described above) [25], and the quality of the resultant FA maps were then assessed in terms of the tensor fitting residual errors [26,27].

To test the capability of achieving high in-plane spatial-resolution with the MUSE technique, DWI (0.375×0.375×5 mm³) and DTI (0.3×0.3×8 mm³) data were acquired with 4-shot interleaved EPI from a healthy volunteer. The DWI data set, consisting of 1 baseline image and 3 images with diffusion gradients at $$b = 800 \frac{\sec}{mm^2}$$

applied along three orthogonal directions, was obtained using an 8-channel coil with the following parameters: number of partial-Fourier over-sampling ky lines 12, in-plane acquisition matrix size 512×268 (i.e., 512×512 after partial-Fourier reconstruction for a 4-shot scan), FOV 19.2× 19.2 cm², axial-plane slice thickness 5 mm, TR 6.5 sec, and TE 74.3 msec. The DTI data set, consisting of 4 baseline images and 15 DWI at $$b = 500 \frac{\sec}{mm^2},$$

was obtained using an 8-channel coil with these scan parameters: number of partial-Fourier over-sampling ky lines 12, in-plane acquisition matrix size 512×268 (i.e., 512×512 after partial-Fourier reconstruction for a 4-shot scan), FOV 15.3× 15.3 cm$^2$, axial-plane slice thickness 8 mm, TR 5 sec, and TE 75.5 msec. The developed MUSE method was used to reconstruct high-resolution DWI and DTI maps, as described above.

To test the reliability of the MUSE method for processing data at different SNR levels, 7 DWI data sets were acquired from a healthy volunteer using an 8-channel coil with b factors of 500, 750, 1000, 1250, 1500, 1750 and $$2000 \frac{\sec}{mm^2}.$$

Each DWI data set consisted of 1 baseline image and 3 images with diffusion gradients applied along three orthogonal directions. Scan parameters included: number of partial-Fourier over-sampling ky lines 12, in-plane acquisition matrix size 384×204 (i.e., 384×384 after partial-Fourier reconstruction for a 4-shot scan), FOV 19.2×19.2 cm$^2$, axial-plane slice thickness 4 mm, TR 5 sec, and TE ranging from 61.7 to 87 msec. Images reconstructed with the MUSE method and the conventional SENSE procedure were compared in terms of the white-matter coefficient of variation (i.e., the ratio of standard deviation to the mean signal intensity within white-matter ROIs).

To further assess the inherent SNR penalty resulting from either MUSE or SENSE reconstruction, three sets of 4-shot spin-echo EPI data (without diffusion sensitizing gradients) were acquired from a healthy volunteer using different receiver coils: 8-channel GE coil; 32-channel GE coil; and 32-channel NOVA coil. Additionally, a 2-shot EPI data set was acquired with an 8-channel GE coil. Scan parameters included: number of partial-Fourier over-sampling ky lines 12, in-plane acquisition matrix size 256×140 (i.e., 256×256 after partial-Fourier reconstruction for a 4-shot scan), FOV 22×22 cm$^2$, axial-plane slice thickness 4 mm, TR 5 sec, and TE 59.3 msec. Without applying diffusion-sensitizing gradients, interleaved EPI images reconstructed directly with 2D FFT (after Nyquist artifact removal) were free from motion-induced aliasing artifact, and thus could be used as the reference to quantify the SNR penalty in either MUSE or SENSE reconstruction.

Using the new MUSE procedure, the aliasing artifacts in interleaved EPI based DWI can be reliably removed, as confirmed from all the acquired data, and the produced images have higher SNR as compared with the SENSE-produced images, as summarized below.

Figure 1B:
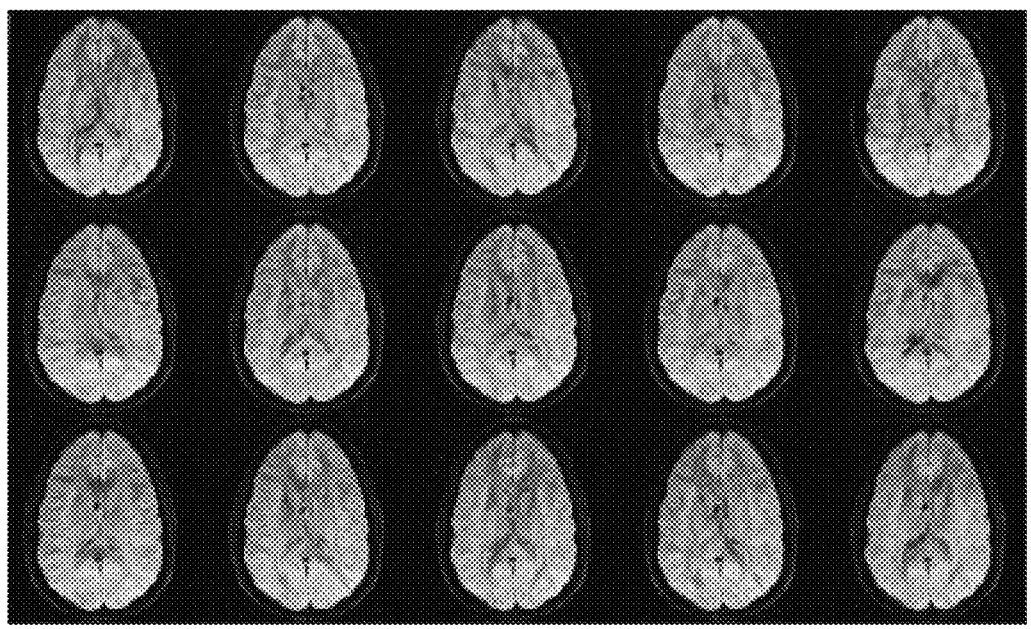
FIG. 1B: Using the MUSE technique, the motion-induced aliasing artifacts can be eliminated.
Figure 1C:
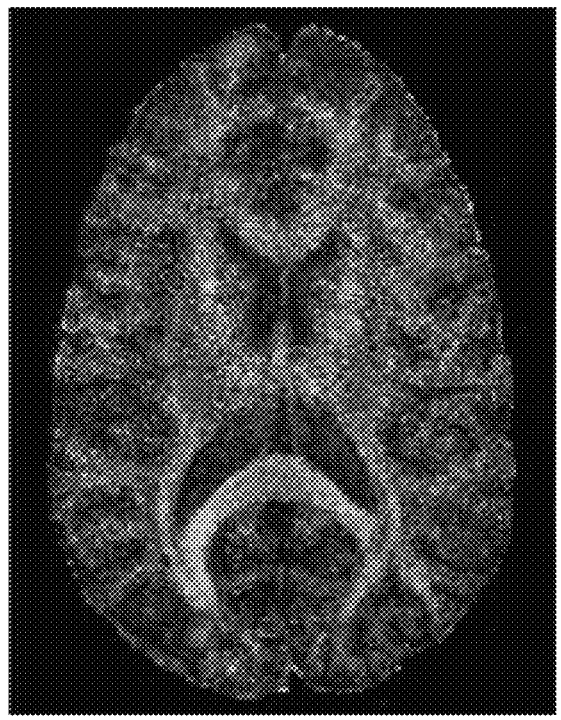
FIG. 1C: The FA map generated from the conventional SENSE reconstruction has a low SNR.
Figure 1D:
FIG. 1D: The SNR is improved in FA map produced with the MUSE technique.

FIG. 1A shows the Nyquist-corrected DWI images produced by the conventional interleaved EPI reconstruction (i.e., a direct k-space data combination followed by 2D FFT), corresponding to 15 directions obtained from one representative participant. As expected, the levels of motion-induced aliasing artifacts vary significantly, depending on the degree of intrascan motion. The ghost-to-signal ratio (GSR) is 0.36±0.13 in images shown in FIG. 1A. FIG. 1B shows that the motion-induced aliasing artifacts can be effectively eliminated using MUSE, regardless of the levels of aliasing artifacts in the raw DWI data. The GSR is 0.08±0.01 in images shown in FIG. 1B. It should be noted that even though the motion-induced aliasing artifacts can also be reduced (GSR: 0.19±0.01) with a conventional SENSE procedure, the resultant images have significantly lower SNRs. FIGS. 1C and 1D compare the FA maps produced with the conventional SENSE reconstruction (i.e., the combination of 4 images produced by applying SENSE to individual segments: [25]) and the new MUSE technique, respectively. Further analyses showed that, for white-matter voxels in this slice, the tensor fitting residual errors achieved with the MUSE method was 53% of that from the conventional SENSE reconstruction [26,27]. It is demonstrated that MUSE-based DWI has a significantly lower noise level as the result of improved conditioning for matrix inversion.

Figure 2A:
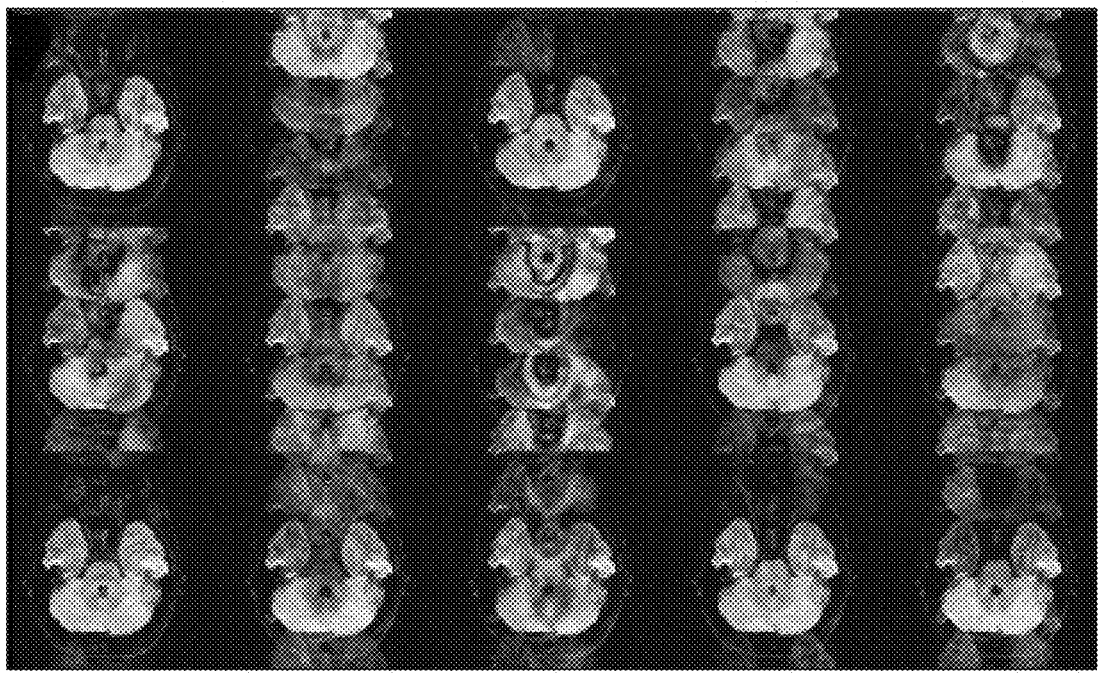
FIG. 2A: Pronounced motion-induced artifacts appear in interleaved DTI when there exist local and nonlinear motions (e.g., in the brainstem).
Figure 2B:
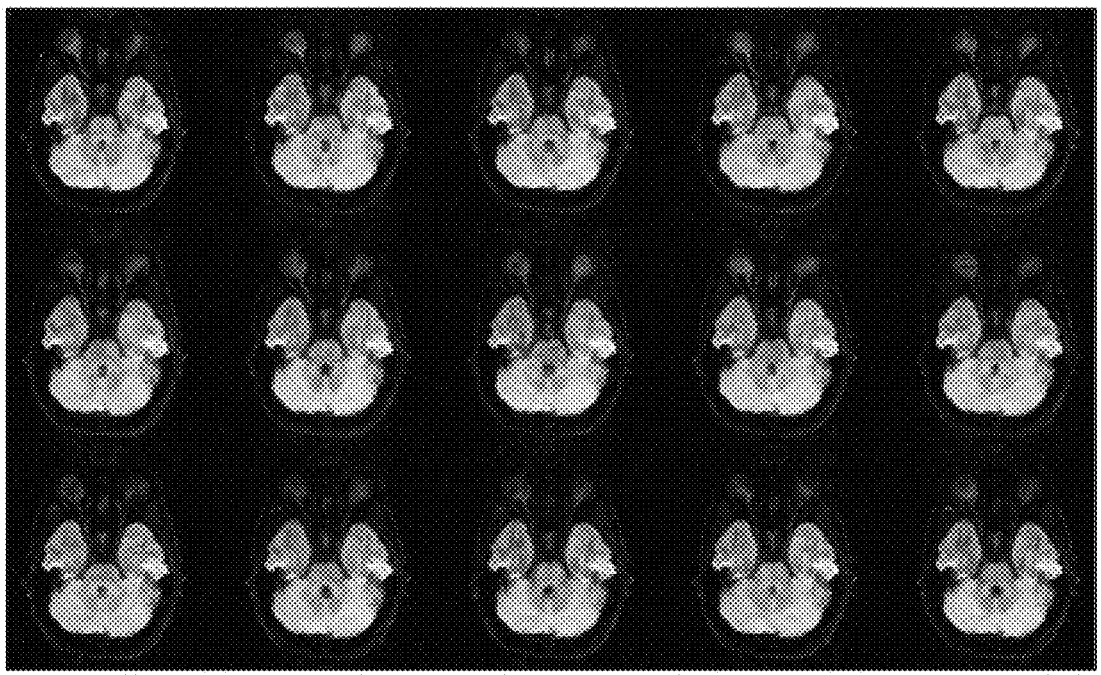
FIG. 2B: The aliasing artifact can be eliminated with the MUSE technique.
Figure 2C:
FIG. 2C: The SNR is low in the FA map produced with the conventional SENSE procedure.
Figure 2D:
FIG. 2D: Using the MUSE technique, the FA map of high-SNR can be achieved.

FIGS. 2A and 2B show the DTI images before and after applying the MUSE procedure, respectively, for another slice that includes the brainstem and eyes where local motion artifacts are prevalent. It can be seen that, because of the local motion, the aliasing artifacts can be highly significant in many of the interleaved DWI images (FIG. 2A, GSR: 0.36±0.22). Furthermore, the aliased signals of the eyes may destructively interfere with the brain images. These aliasing artifacts can all be effectively eliminated by the MUSE procedure, as demonstrated in FIG. 2B (GSR: 0.05±0.01). Again, even though the motion-induced aliasing artifact can also be suppressed (GSR: 0.13±0.01) with the conventional SENSE reconstruction, the resultant DTI images and FA map have lower SNR (FIG. 2C) as compared with the MUSE produced results (FIG. 2D). For white-matter voxels in this slice, the tensor fitting residual errors [26,27] achieved with the MUSE method was 69% of that from the conventional SENSE reconstruction.

For a 2D 4-shot EPI of 256×256 matrix obtained with an 8-channel coil, the data processing time was about 83 sec (including 20 sec for an iterative 2D phase-cycled reconstruction and Nyquist artifact removal; 17 sec for initial SENSE estimation of shot-to-shot phase variation, 10 sec for the total variation based noise reduction, and 36 sec for the final MUSE reconstruction) with Matlab programs running in an Apple Macbook Pro (2.7 GHz intel core i7 CPU; 8 GB DDR3 memory). Note that the computation time can be reduced by performing pre-processing steps (including 2D phase-cycled reconstruction, initial SENSE based estimation of shot-to-shot phase variation, and total variation based smoothing) only in the central portion of the k-space data. For example, if the pre-processing steps were carried in the central 64×64 k-space matrix and the calculated phase errors maps were subsequently interpolated to 256×256 matrices for the final MUSE reconstruction, then the total data processing time was about 50 sec per slice (including 4 sec for an iterative 2D phase-cycled reconstruction and Nyquist artifact removal; 3 sec for initial SENSE estimation of shot-to-shot phase variation, 7 sec for the total variation based noise reduction, and 36 sec for the MUSE reconstruction).

Figure 3A:
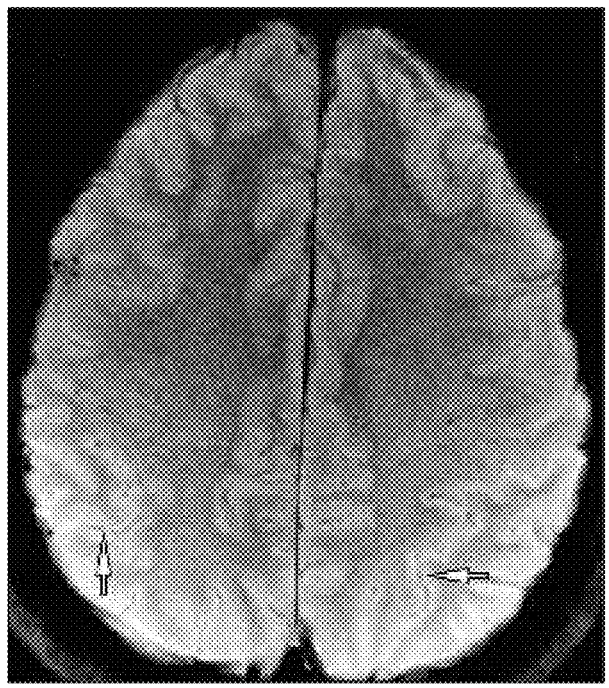
FIG. 3A is an MRI image of DWI data of high in-plane resolution $$\left(\text{voxel size: } 0.375 \times 0.375 \times 5 \, mm^3; b = 800 \frac{\sec}{mm^2}\right)$$
Figure 3B:
FIG. 3B is an MRI image with a low-resolution reconstruction of the same data set (voxel size: 1.5×1.5×5 mm³) cannot reveal the same anatomic details.

FIG. 3A shows a MUSE-based DWI image at high in-plane resolution (voxel size: 0.375×0.375×5 mm$^3$; matrix size: 512×512), where fine anatomic features are visible. In contrast, the low-resolution version of the same image (FIG. 3B: voxel size: 1.5×1.5×5 mm$^3$; matrix size: 128×128), reconstructed from only the central portion of the k-space data, has significantly lower anatomic resolvability (as indicated by arrows). FIG. 4A shows an FA map with high in-plane resolution (0.3×0.3×8 mm$^3$) generated by the developed MUSE method. The voxels inside the white box are displayed in FIG. 4B, where distinct FA patterns, likely between white matter and gray matter (indicated by green and red arrows), are visible. FIGS. 4C and 4D show the contours of the indicated green and red voxels overlaid onto the mean DWI and T2*-weighted EPI maps (i.e., the non-diffusion-weighted baseline EPI), respectively, suggesting that white and gray matter FA patterns can be differentiated with the MUSE-based high-resolution DTI. Images shown in FIGS. 3 and 4 indicate that the developed MUSE method enables high-resolution DWI and can provide information that is usually not available at low in-plane spatial-resolution.

FIGS. 5A and B compare the MUSE- and SENSE-produced DWI maps corresponding to b factors ranging from $$500 \text{ to } 2000 \frac{\text{sec}}{\text{mm}^2} \text{ at a } 250 \frac{\text{sec}}{\text{mm}^2} \text{ step.}$$

It can be seen that the motion-induced aliasing artifacts can all be effectively removed with the MUSE method regardless of the SNR level, and the MUSE method is less susceptible to undesirable noise amplification as compared with the SENSE reconstruction. The magnitude average of all 7 MUSE-DWI and the magnitude average of all SENSE-DWI are shown in FIGS. 5C and 5D, respectively, for an easy visualization of the SNR difference between these two reconstruction methods. The white-matter coefficient of variation (i.e., the ratio of standard deviation to the mean signals in a white-matter ROIs) in images reconstructed with the MUSE and SENSE methods are shown by black and yellow bars, respectively, in FIG. 5E. The SNR values for the MUSE-based DWI images, measured by the ratio of white-matter signals to the background noises, are 8.5, 6.5, 5.0, 3.9, 3.4, 2.9, and 2.4. These data suggest that the MUSE reconstruction is superior to conventional SENSE reconstruction even for DWI data with very low SNR.

Non-diffusion-weighted interleaved EPI images reconstructed directly with 2D FFT were used as the reference to measure the SNR penalty resulting from either MUSE or SENSE reconstruction. First, for data obtained with an 8-channel GE coil, the white-matter coefficient of variation in 4-shot MUSE images was 3.1% higher than that obtained with 2D FFT, and the white-matter coefficient of variation in 4-shot SENSE images was 23.3% higher than that obtained with 2D FFT. Second, with the same 8-channel GE coil, the white-matter coefficient of variation in 2-shot MUSE images was 0.4% higher than that obtained with 2D FFT, and the white-matter coefficient of variation in 2-shot SENSE images was 14.6% higher than that obtained with 2D FFT. Third, for data obtained with a 32-channel GE coil, the white-matter coefficient of variation in 4-shot MUSE images was 1.2% higher than that obtained with 2D FFT, and the white-matter coefficient of variation in 4-shot SENSE images was 16.7% higher than that obtained with 2D FFT. Fourth, using a 32-channel NOVA coil, the white-matter coefficient of variation in 4-shot MUSE images was 8.5% higher than that obtained with 2D FFT, and the white-matter coefficient of variation in 4-shot SENSE images was 41.0% higher than that obtained with 2D FFT. These data suggest that the SNR penalty resulting from the MUSE reconstruction is generally not significant for 2-shot and 4-shot EPI, and is always smaller as compared with the SENSE reconstruction.

In summary, MUSE can be a general and effective approach to enable high-resolution DWI through multi-shot acquisitions. The developed MUSE technique produces multi-shot DWI data with higher spatial resolution and fidelity, as compared with single-shot acquisition. In comparison to the conventional navigator-based interleaved DWI, the new MUSE technique, which requires neither navigator nor reference echoes, also has several advantages. First, the imaging throughput of navigator-less interleaved DWI is higher than that of navigator-based interleaved DWI. Second, unlike navigator-based correction which could fail when the motions differ between navigation, the newly developed MUSE method can inherently measure and correct phase errors. Similar to the variable-density spiral imaging based DWI [20,21,22], our MUSE method is capable of inherently estimating both linear and nonlinear phase variations directly from the acquired multi-shot DWI data, but without requiring any pulse sequence modification.

A limitation of some embodiments of the MUSE method is that the number of EPI segments cannot be higher than the number of coils; otherwise the phase variation maps cannot be estimated with the conventional SENSE procedure (i.e., step 3 described in the Methods section). It should be noted that, as compared with the conventional SENSE reconstruction, the MUSE procedure has an improved matrix inversion conditioning even when the number of EPI segments is not significantly smaller than the number of coils. For example, as demonstrated in the human brain data, robust high-resolution DWI can be obtained from a 4-shot interleaved EPI acquisition using an 8-channel receiver coil.

The MUSE algorithm is different from existing parallel imaging based motion correction methods that were designed to correct large scale motion in non-diffusion-weighted MRI [28]. In contrast, in some embodiments, MUSE addresses issues related to shot-to-shot phase inconsistencies in interleaved DWI due to small-scale (e.g., sub-voxel) motions, while assuming that there is no large-scale intrascan motion (i.e., significantly larger than 1 voxel) and the magnitude signals remain constant across multiple EPI segments (FIG. 9). This condition is largely met in most scans with cooperative subjects. In the presence of very large scale motion, it would be inappropriate to assume that the magnitude signals remain constant across multiple EPI segments. In this case, the MUSE algorithm would need to be further modified or expanded to accommodate for large-scale intrascan motion [29] (FIG. 10). It should also be noted that the developed method is designed to address the phase variations among EPI segments, but not those within each individual segment.

Figure 10A:
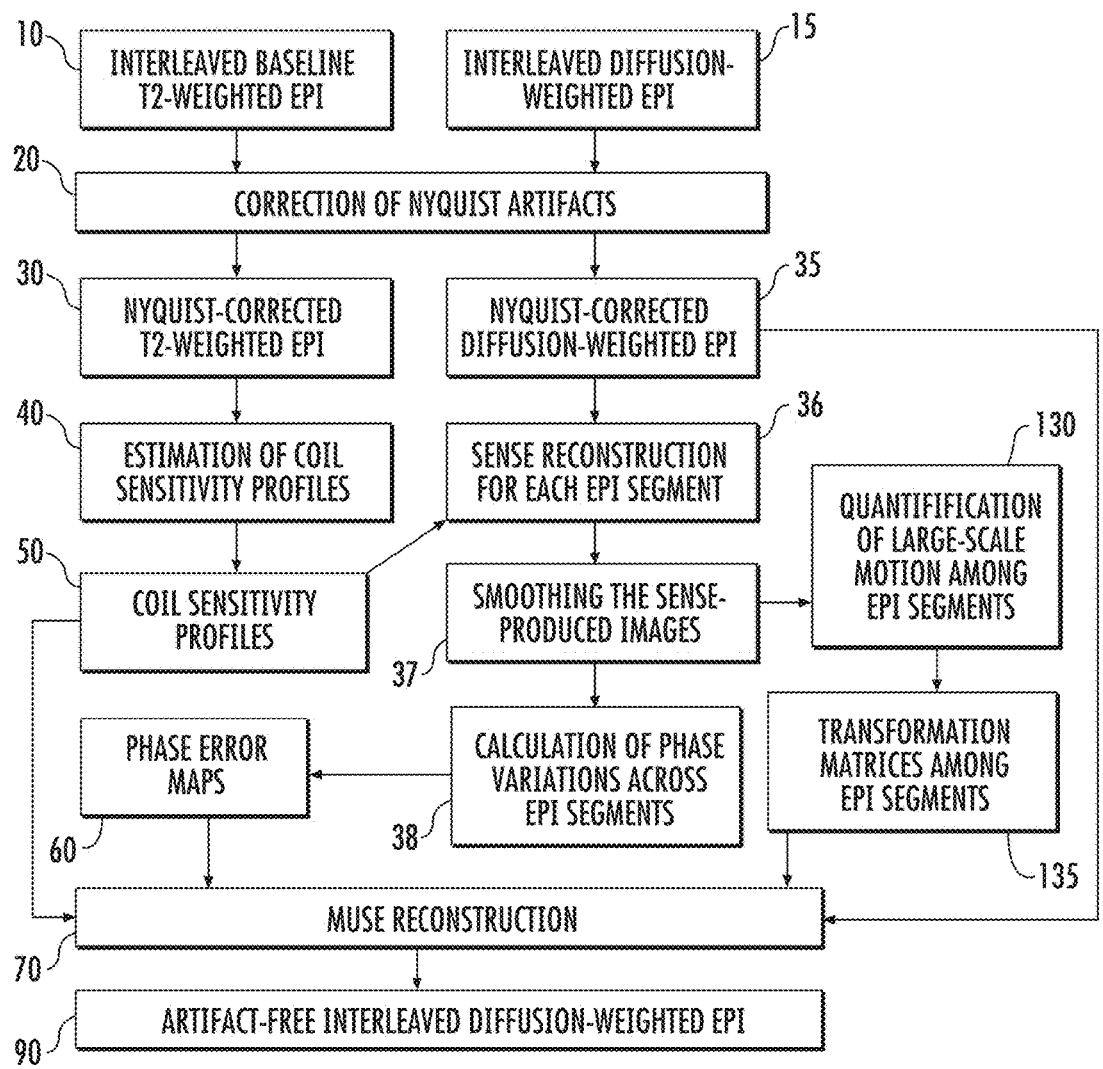
FIG. 10A is a flow chart of exemplary actions that can be performed to generate MRI images according to some embodiments of the present invention.

The MUSE algorithm can be further expanded to accommodate for large-scale intrascan motion as shown, for example, in FIGS. 10A-10F. To achieve this, the acquired data (blocks 10, 15 or 10, 15e or 10, 15p or 15f) can be processed. FIG. 10A illustrates the following steps, using 2-shot EPI based DWI as an example. First, the phase-cycled reconstruction procedure [30] can be used to measure the phase errors resulting from odd-even echo inconsistencies in the baseline (i.e., T2-weighted) image (block 10), and the measured information is then used to suppress the Nyquist artifacts in both baseline and diffusion-weighted images (blocks 20, 30, 35). Second, the coil-sensitivity profiles are estimated (blocks 40, 50) from the baseline (Nyquist-corrected) T2-weighted images (block 30).

With reference to FIG. 10A, third, using the conventional SENSE reconstruction procedure (block 36), two full-FOV images (or N full-FOV images for N-shot EPI based DWI) are reconstructed from two DWI segments (or N DWI segments for N-shot EPI based DWI), and the shot-to-shot phase variations are calculated with Equation 7, where the total variation algorithm is used to smooth the complex images (block 37). Phase variations can be calculated across EPI segments (block 38) and phase error maps can be generated (block 60). Fifth, the translational and rotational motion between two SENSE-produced images (or N SENSE-produced images for N-shot EPI scans) are estimated with the previously reported procedure (block 130). See, Eddy W F, Fitzgerald M, Noll D C. 1996. Improved image registration by using Fourier interpolation. Magn Reson Med. 36:923-931; and Maas L C, Frederick B D, Renshaw P F. 1997. Decoupled automated rotational and translational registration for function MRI time series data: the DART registration algorithm. Magn Reson Med. 37:131-139. Sixth, the translational and rotational information is incorporated into the modified MUSE equations to unfold the signals from overlapping voxels (blocks 135, 70). For example, Equations 9 and 10 described in the previous paragraph are modified to accommodate for intrascan motion, as shown in Equations 11 and 12 with M representing the transformation matrix (including rotation and translation) between 2 DWI segments using the first segment as a position reference. Seventh, through unfolding overlapping voxels in all image-domain columns simultaneously with Equations 11 and 12, artifact-free and high-SNR DWI can be reconstructed with this modified MUSE procedure (block 90).

$$u_j(x,y) = \left[S_j(x,y)\frac{TV(p_s(x,y))}{|TV(p_s(x,y))|}\right]D(x,y) + \left[S_j\left(x, y+\frac{FOV_y}{2}\right)\right. \tag{11}$$

$$\left.\frac{TV\left(p_s\left(x, y+\frac{FOV_y}{2}\right)\right)}{\left|TV\left(p_s\left(x, y+\frac{FOV_y}{2}\right)\right)\right|}\right]D\left(x, y+\frac{FOV_y}{2}\right)$$

$$v_j(x,y) = \left[M(S_j(x,y))\frac{TV(M(q_s(x,y)))}{|TV(M(q_s(x,y)))|}\right] \tag{12}$$

$$M(D(x,y)) - \left[M\left(S_j\left(x, y+\frac{FOV_y}{2}\right)\right)\right.$$

$$\left.\frac{TV\left(M\left(q_s\left(x, y+\frac{FOV_y}{2}\right)\right)\right)}{\left|TV\left(M\left(q_s\left(x, y+\frac{FOV_y}{2}\right)\right)\right)\right|}\right]M\left(D\left(x, y+\frac{FOV_y}{2}\right)\right)$$

Figure 6:
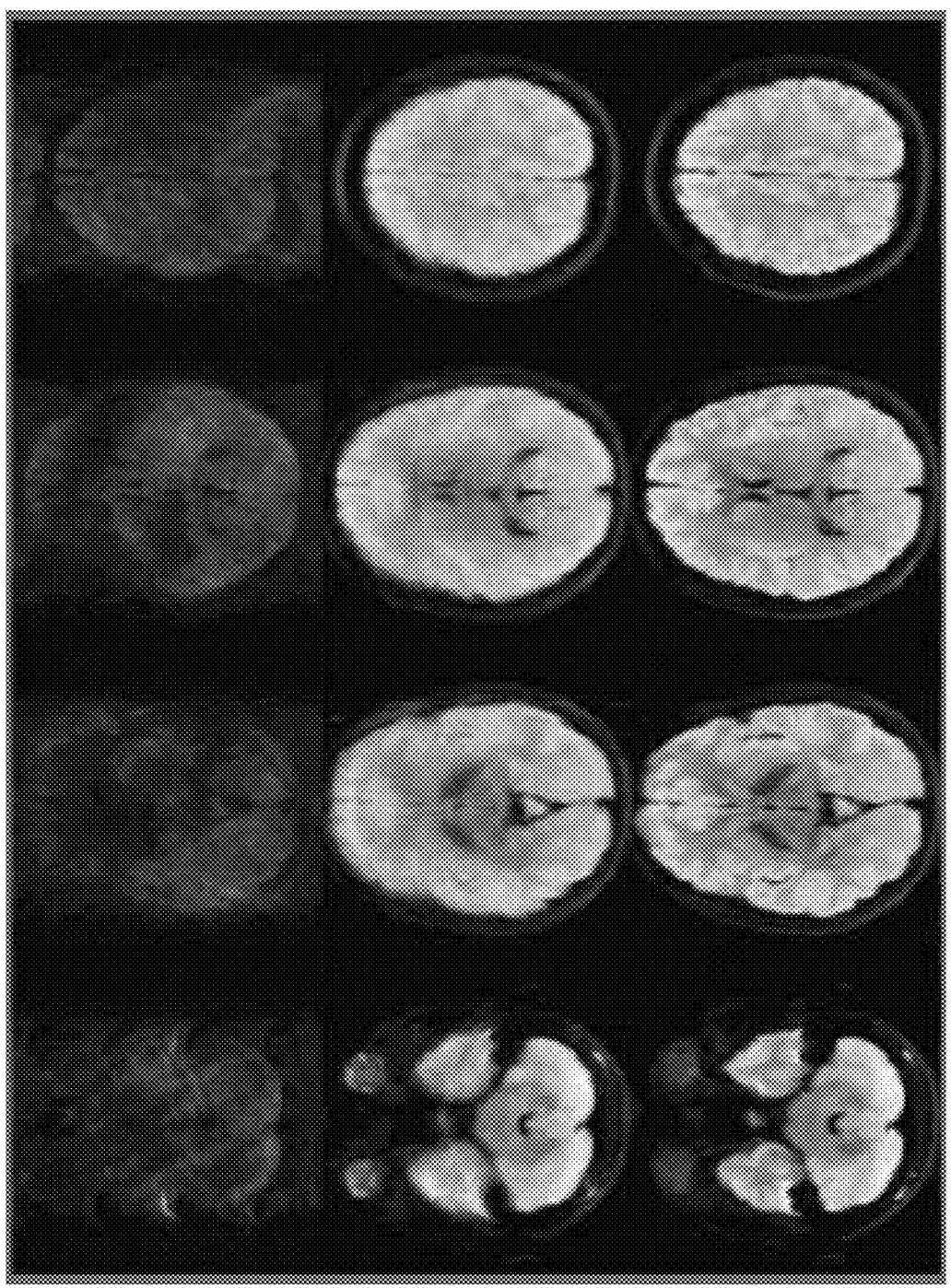
FIG. 6 shows three rows of MRI images: The top row of FIG. 6 shows the uncorrected 4-shot DWI, of 4 axial slices, in the presence of pronounced intrascan motion. The middle row of FIG. 6 shows the images reconstructed with the original MUSE procedure. It can be seen that the aliasing artifact is reduced in MUSE-produced images as compared with the uncorrected images, but the residual blurring artifact due to the intra-scan motion is still visible. Using the improved MUSE procedure images, the bottom row of FIG. 6 shows that residual artifacts can be effectively eliminated, and the reconstructed images have high-quality and high-SNR.

The modified MUSE algorithm described with respect to FIG. 10A, accommodating large-scale intrascan motion, was experimentally verified with human MRI data acquired from a 3 Tesla system equipped with an 8-channel head RF coil, using a 4-shot EPI based DWI pulse sequence. The healthy volunteer was instructed to move his head during the DWI scans, thus creating pronounced artifacts associated with the large-scale intrascan motion. The original MUSE procedure (i.e., similar to Equation 9 and 10 but for 4-shot EPI) and the modified MUSE procedure (i.e., similar to Equations 11 and 12 but for 4-shot EPI) were used to suppress the artifacts. The image quality was compared as shown in FIG. 6. The top row of FIG. 6 shows the uncorrected 4-shot DWI, of 4 axial slices, in the presence of pronounced intrascan motion. The middle row of FIG. 6 shows the images reconstructed with the original MUSE procedure. It can be seen that the aliasing artifact is reduced in MUSE-produced images as compared with the uncorrected images, but the residual blurring artifact due to the intra-scan motion is still visible. Using the improved MUSE procedure (the bottom row of FIG. 6), residual artifacts can be effectively eliminated, and the reconstructed images have high-quality and high-SNR.

Even though the MUSE procedure is particularly valuable in enabling high-resolution and high-quality interleaved DWI, the concept of multiplexed parallel imaging can also be applied to eliminate motion-induced artifacts in interleaved high-resolution DWI and DTI with other Cartesian or non-Cartesian pulse sequences (such as interleaved fast spin-echo imaging and/or interleaved spiral imaging).

It should also be noted that the MUSE can also be applied to improve the quality for other types of pulse sequences where high spatial resolution is desired, such as interleaved EPI based functional MRI (fMRI) in the presence of phase variations over time due to physiological motions or magnetic field drifting. FIG. 9B illustrates an example of such a protocol similar to FIG. 9A but modified for fMRI according to embodiments of the present invention.

Figure 10B:
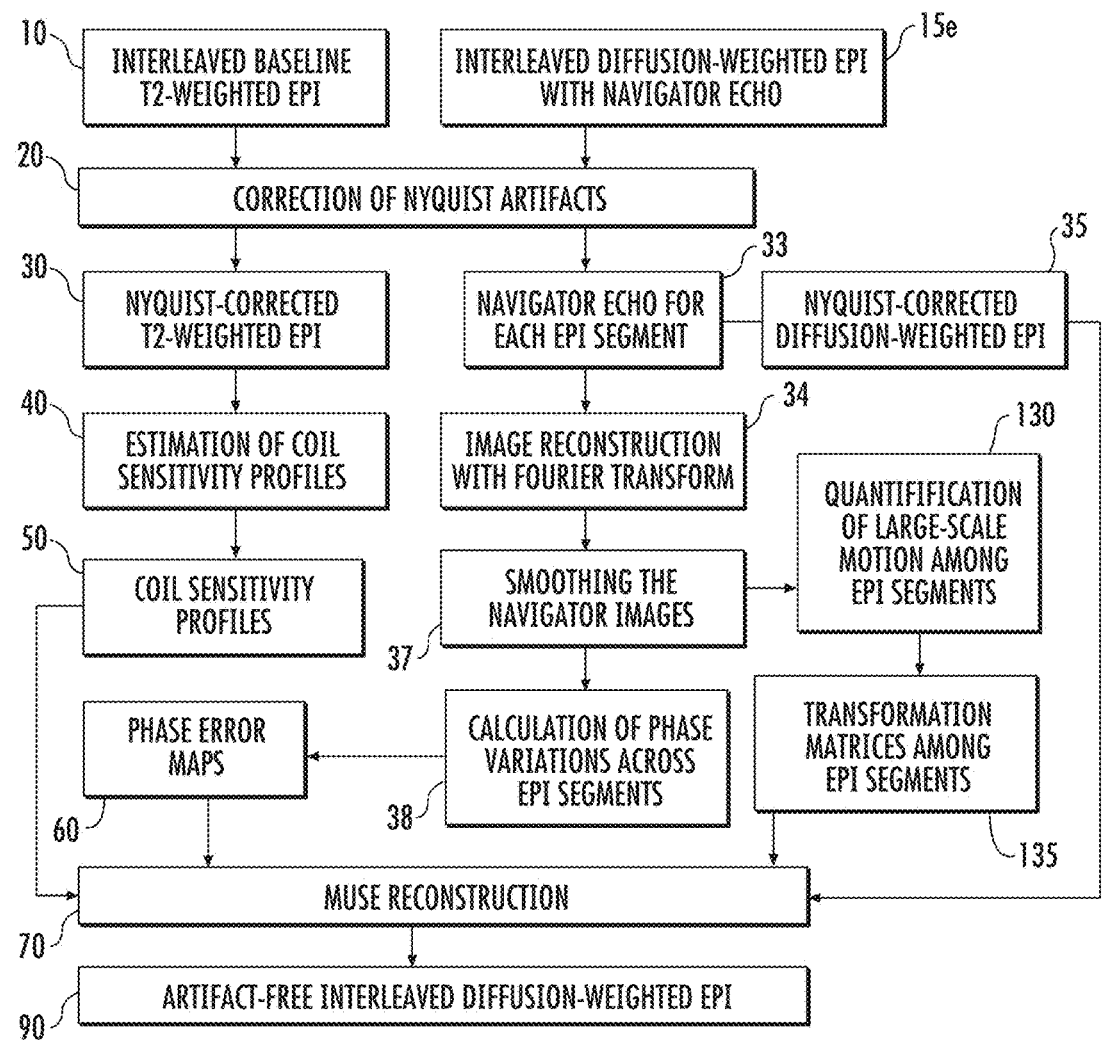
FIG. 10B is a flow chart of exemplary actions that can be performed to generate MRI images using navigator echoes according to some embodiments of the present invention.

FIG. 10B illustrates a flow chart of exemplary actions that can be performed to generate MRI images using navigator echoes according to some embodiments of the present invention. As shown, the analysis can include interleaved diffusion-weighted EPI with navigator echo (block 15e), yielding a navigator echo for each EPI segment (block 33) and image reconstruction with FT (Fourier Transform) (block 34) as an alternative to the SENSE protocol with smoothing (block 37), calculation of phase variations (block 38), and phase error maps (block 60) for the MUSE reconstruction (block 70).

Figure 10C:
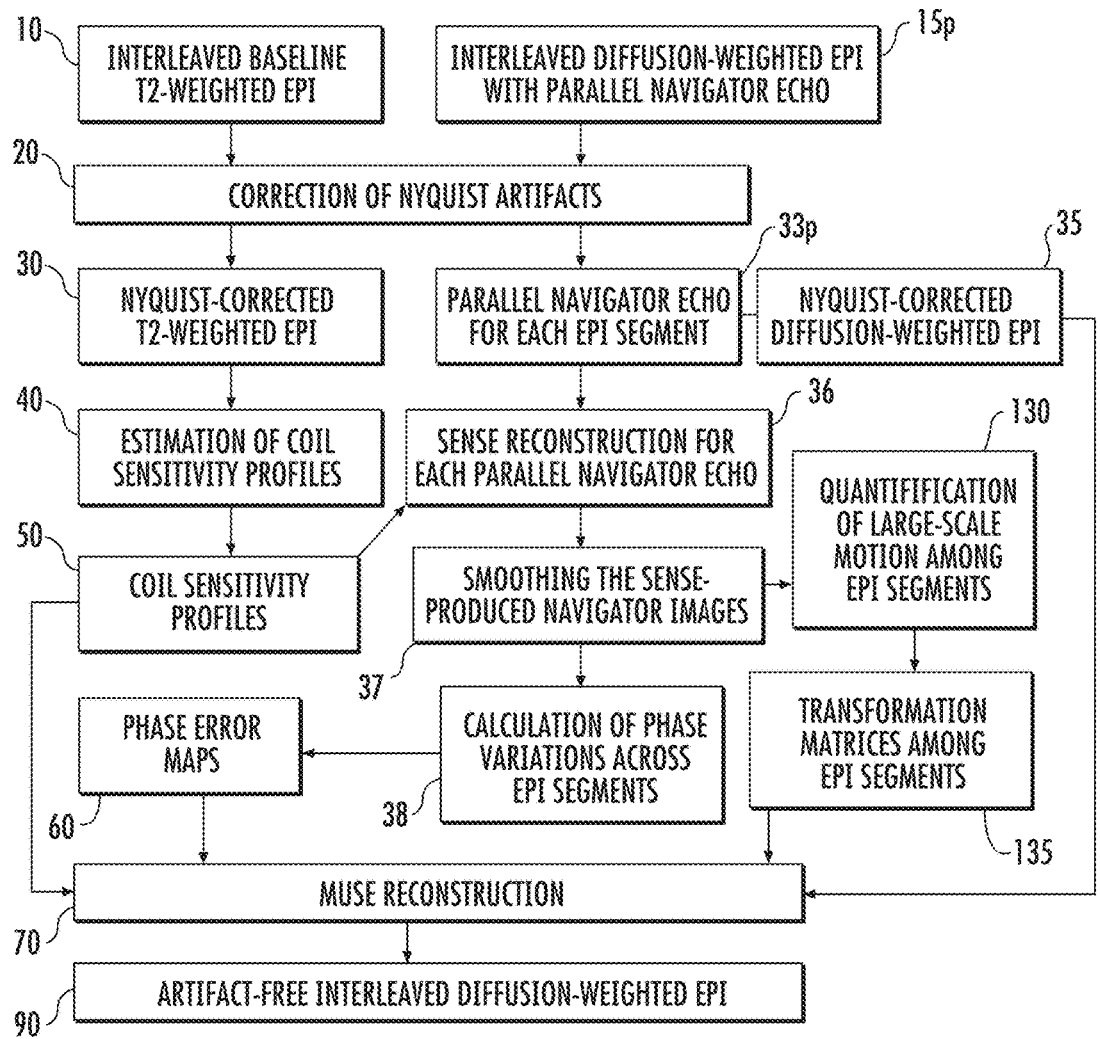
FIG. 10C is a flow chart of exemplary actions that can be performed to generate MRI images using parallel navigator echoes according to some embodiments of the present invention.

FIG. 10C is a flow chart of exemplary actions that can be performed to generate MRI images using interleaved diffusion-weighted EPI with parallel navigator echo (block 15p) yielding a parallel navigator echo for each EPI segment (block 33p) according to some embodiments of the present invention with parallel imaging (e.g., SENSE) reconstruction (block 36), smoothing (block 37), calculation of phase variations (block 38) and phase error maps (block 38) for the MUSE reconstruction (block 70).

Figure 9A:
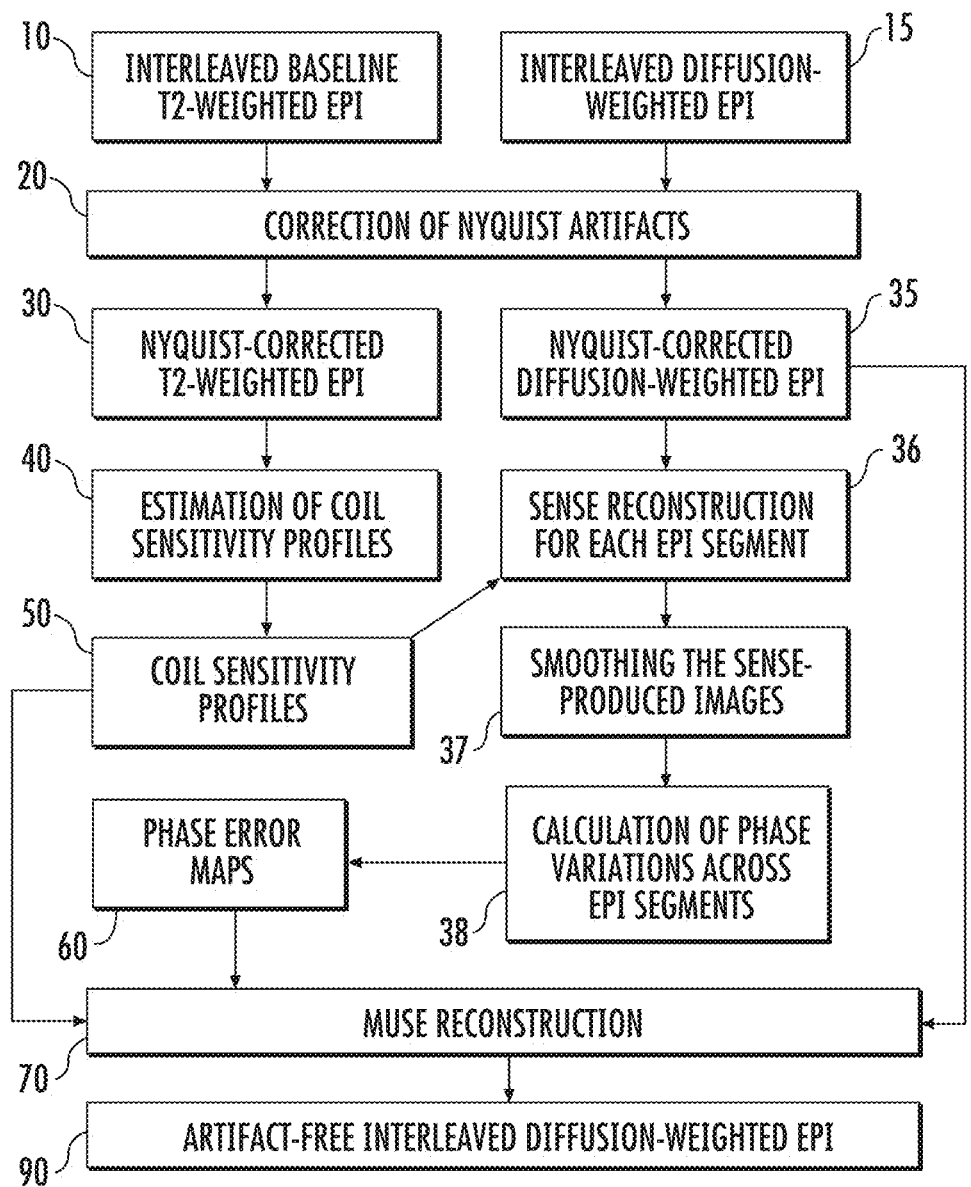
FIG. 9A is a flow chart of exemplary actions that can be performed to generate MRI images according to embodiments of the present invention.
Figure 9B:
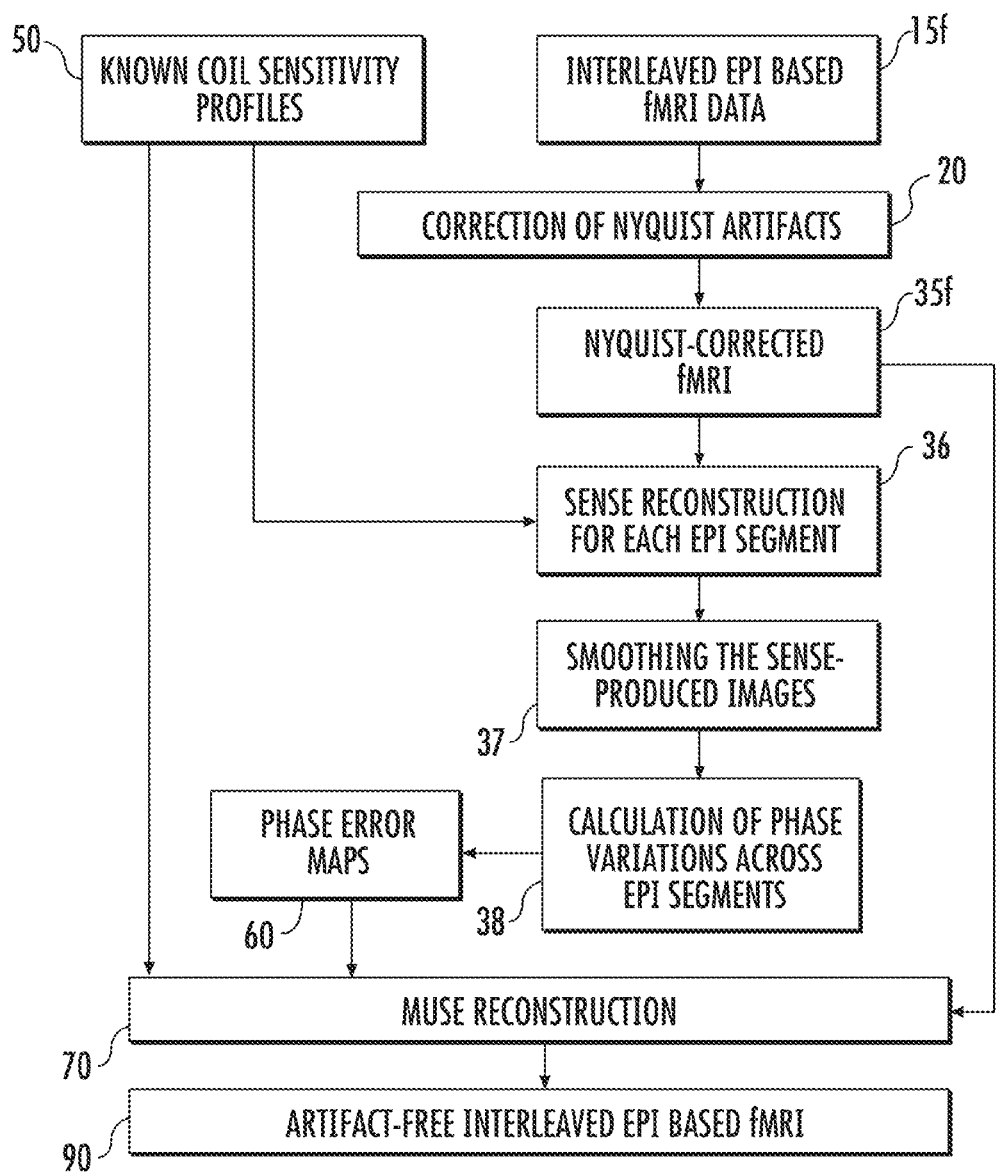
FIG. 9B is a flow chart of exemplary actions that can be performed to generate non-DWI images according to embodiments of the present invention.

Protocols similar to FIGS. 10B, 10C without the quantification of large-scale motion blocks 130, 135 may also be used with navigator echoes, similar to FIG. 9A.

Figure 10D:
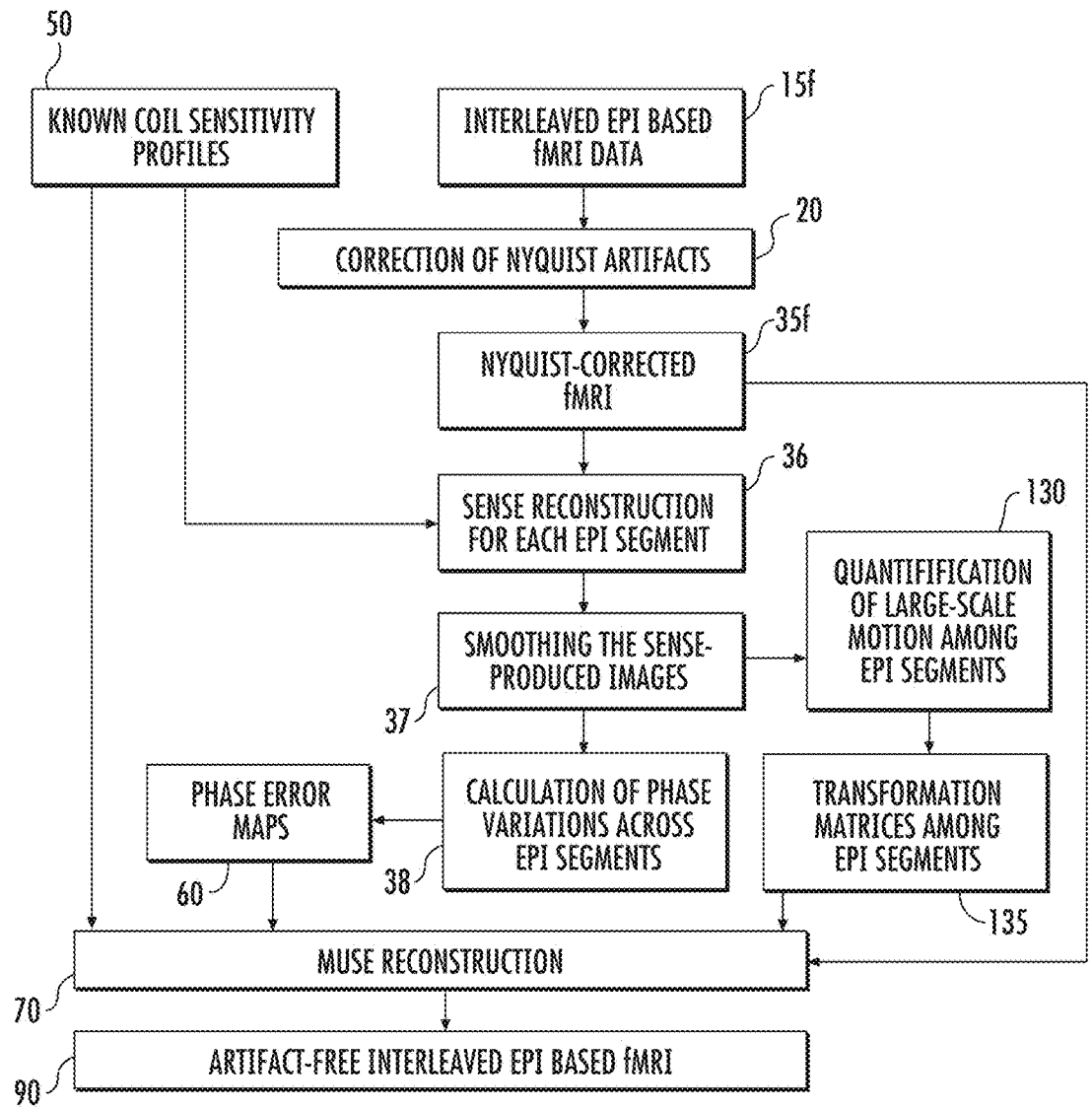
FIG. 10D is a flow chart of exemplary actions that can be performed to generate MRI images using fMRI data according to some embodiments of the present invention.
Figure 10E:
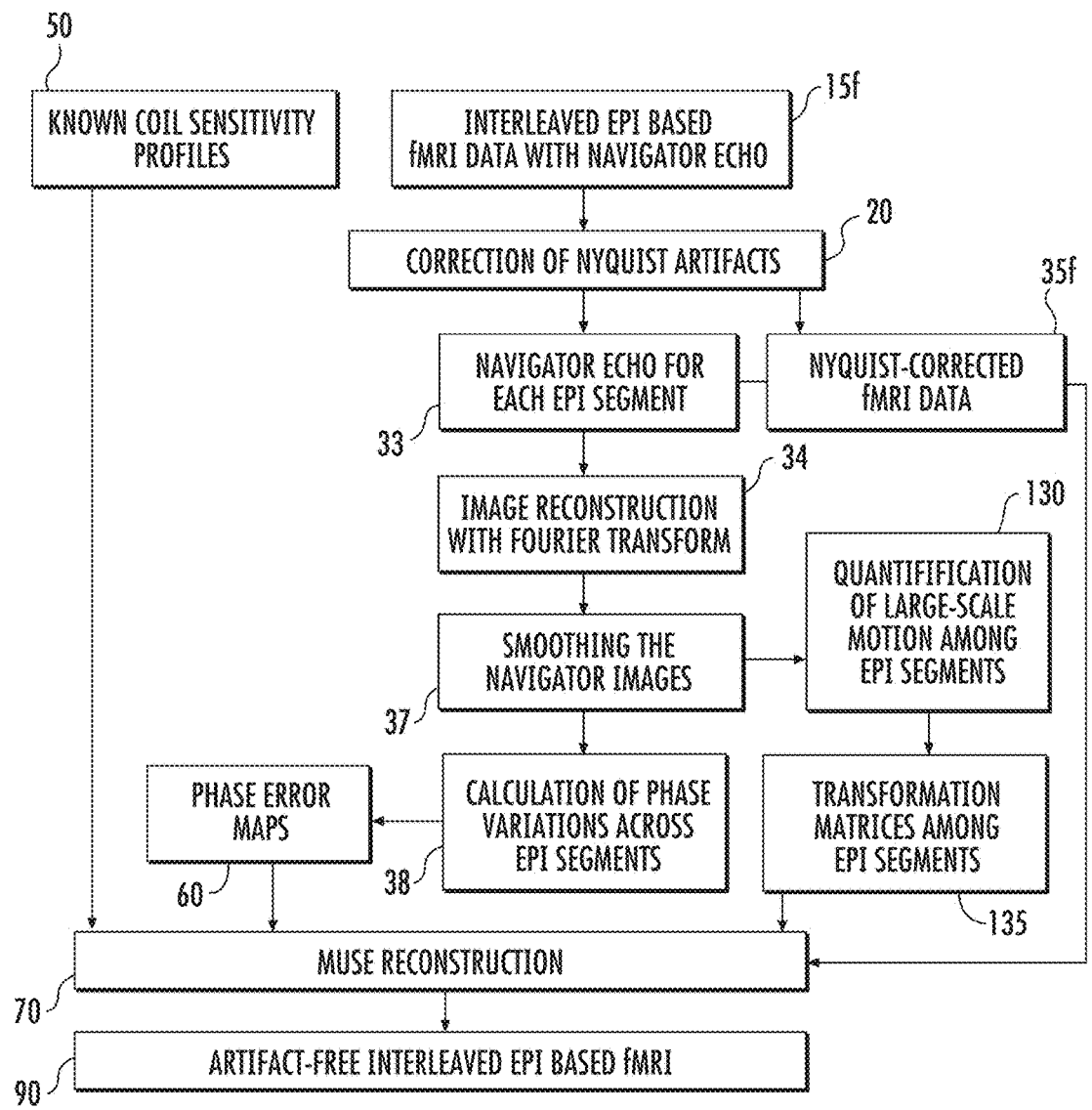
FIG. 10E is a flow chart of exemplary actions that can be performed to generate MRI images using fMRI data and navigator echoes according to some embodiments of the present invention.
Figure 10F:
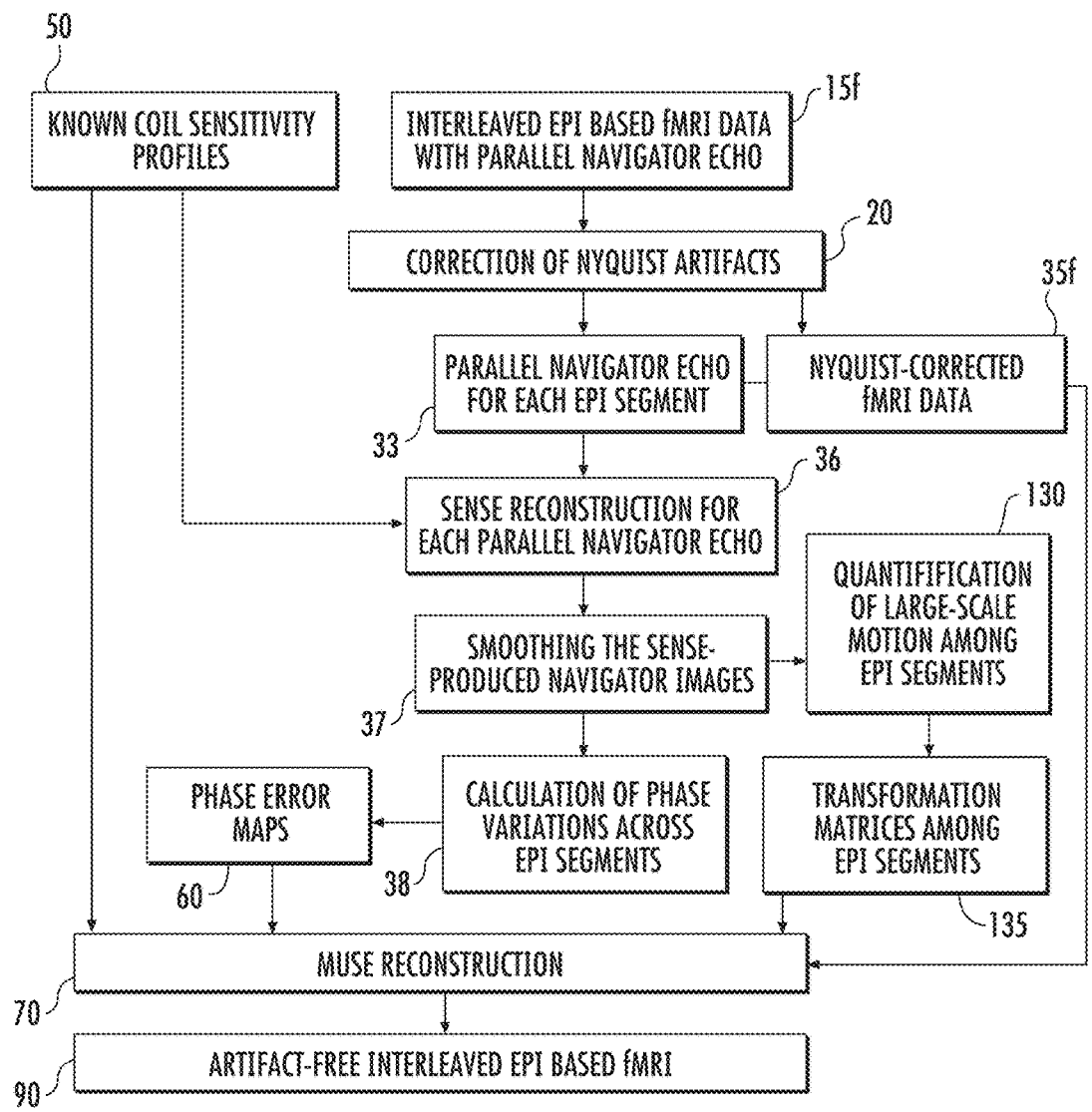
FIG. 10F is a flow chart of exemplary actions that can be performed to generate MRI images using fMRI data and parallel navigator echoes according to some embodiments of the present invention.

The MUSE reconstruction module can be used for fMRI and other non-DWI/DTI image data using the same or substantially similar post-processing procedure described above as shown in FIGS. 9B and 10D-10F. It is noted that there is no baseline T2-EPI in fMRI studies. Coil sensitivity profiles provided by an additional calibration scan, which is a standard procedure, can alternatively be used to provide known coil sensitivity profiles (block 50). Interleaved EPI based fMRI data can be acquired (block 15f) and corrected for Nyquist artifacts (block 20). FIG. 9B illustrates an embodiment which processes fMRI data but does not include navigator echoes and does not include the large scale motion adjustment (compare FIGS. 10D-10F). FIG. 10D does not include navigator echoes but does adjust for large scale motion amount EPI segments (block 130, block 135) for the MUSE reconstruction (block 70), similar to FIG. 10A. FIG. 10E uses interleaved EPI based fMRI data with navigator echo (block 150 and a navigator echo for each EPI segment (block 33) with FT image reconstruction (block 34) similar to FIG. 10B for DWI data. FIG. 10F uses interleaved EPI based fMRI data with parallel navigator echo (block 151) for parallel navigator echo for each EIP segment (block 33) and SENSE reconstruction (block 36) similar to FIG. 10C for DWI data.

Experimental comparisons have been performed for 1) the MUSE reconstruction, 2) the conventional segmented EPI reconstruction (i.e., a simple 2D Fourier transform), and 3) the SENSE-based reconstruction of 4-shot interleaved EPI based fMRI data, in terms of the resultant temporal fluctuation noise level and time-domain SNR level, as shown in FIG. 7.

Figure 7C:
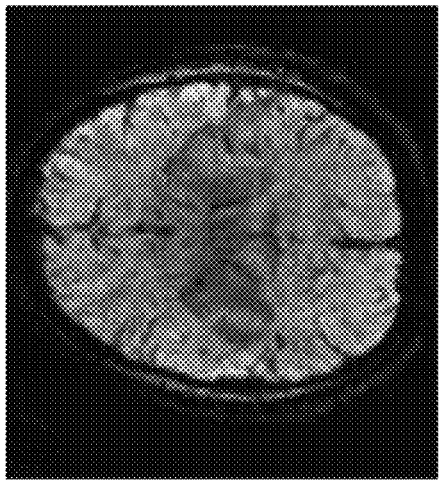
FIG. 7: The top row of FIG. 7 compares the temporal fluctuation noise levels in images obtained with (7A) the conventional segmented EPI reconstruction of 4-shot EPI data, (7B) the magnitude summation of 4 consecutive SENSE-produced images, and (7C) the MUSE algorithm. It can be seen that the MUSE-based reconstruction produces data with the lowest time-domain fluctuation. The bottom row of FIG. 7 compares the time-domain SNR levels in images obtained with (7D) the conventional segmented EPI reconstruction, (7E) the SENSE-based reconstruction, and (7F) the MUSE algorithm.
Figure 7F:
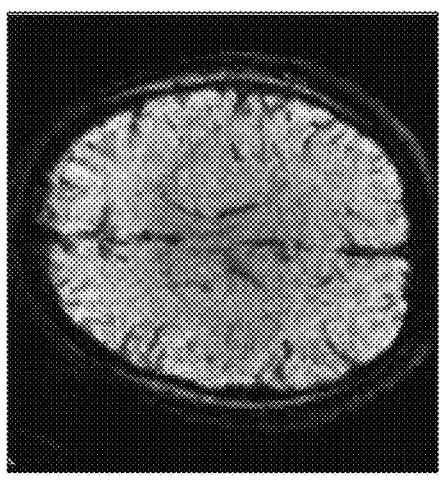
Figure 7B:
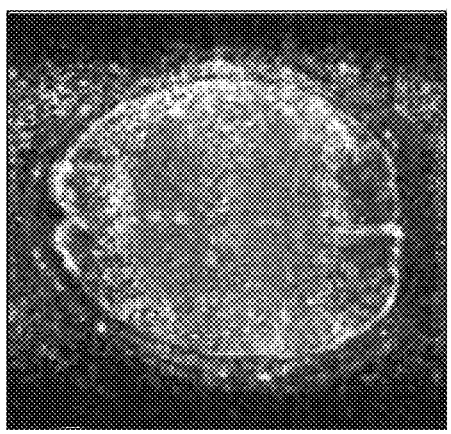
Figure 7E:
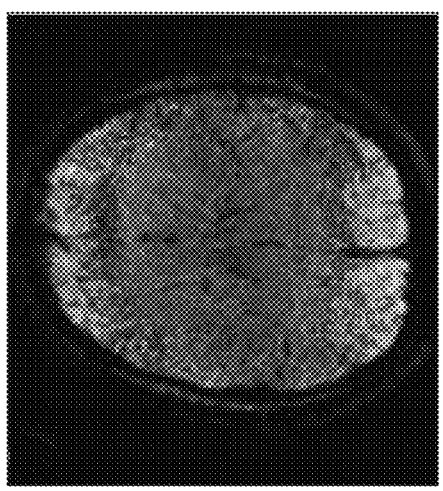
Figure 7A:
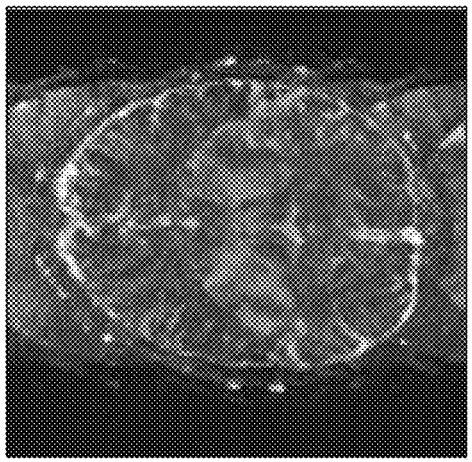
Figure 7D:
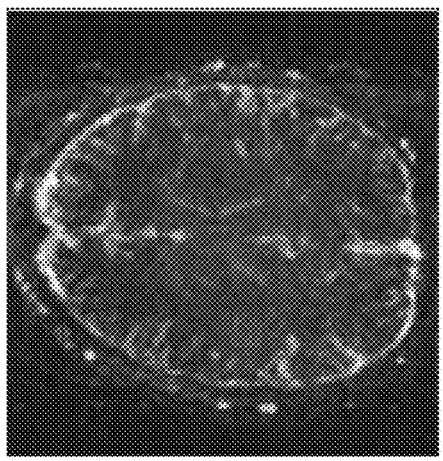

The top row of FIG. 7 compares the temporal fluctuation noise levels in T2*-weighted images (e.g., used in most functional MRI studies) obtained with three different protocols: the conventional segmented EPI reconstruction of 4-shot EPI data (FIG. 7A), the magnitude summation of 4 consecutive SENSE-produced images (FIG. 7B), and the MUSE algorithm (FIG. 7C). It can be seen that the MUSE-based reconstruction produces data with the lowest time-domain fluctuation. The bottom row of FIG. 7 compares the time-domain SNR levels in images obtained with the conventional segmented EPI reconstruction (FIG. 7D), the SENSE-based reconstruction (FIG. 7E), and the MUSE algorithm (FIG. 7F). The results show that the highest time-domain SNR can be achieved with the MUSE algorithm, as compared with the segmented EPI reconstruction and SENSE reconstruction.

The MUSE algorithm is capable of estimating shot-to-shot phase variations and intrascan motion inherently from the initial SENSE reconstruction of multi-shot interleaved EPI data, without relying on any navigator echo or pulse sequence modification. It should be noted that the MUSE algorithm is actually compatible with interleaved DWI pulse sequences that have navigator echo acquisition embedded. When the navigator echoes are available, the shot-to-shot phase variations and intrascan motion may be derived from the embedded navigator echoes and then used in the MUSE reconstruction based on either Equations 9 and 10 (in the absence of large-scale intrascan motion) or Equations 11 and 12 (in the presence of large-scale intrascan motion) to produce artifact-free images. As compared with the conventional navigator-echo based interleaved DWI reconstruction [9,10,11,12,13,14], the integration of MUSE and navigator echo information explicitly uses the coil sensitivity profiles to significantly improve the matrix inversion conditioning when unfolding the aliased signals. Therefore, the MUSE-based reconstruction of interleaved DWI data, with phase information estimated from navigator echoes, is mathematically more stable than the existing navigated DWI reconstruction [9,10,11,12,13,14]. Another advantage of integrating the MUSE reconstruction algorithm and the navigated DWI acquisition is that the number of EPI interleaves is allowed to be equal to or greater than the number of RF coil channels, since an initial SENSE reconstruction (that provides shot-to-shot phase variations in navigator-less MUSE) can be avoided with the integrated algorithm. Experiments have demonstrated the feasibility of integrating the MUSE reconstruction algorithm and the 8-shot DWI acquisition with a navigator-echo, using a 3 Tesla system equipped with an 8-channel head coil, as shown in FIG. 8.

The top row of FIG. 8 shows three raw DWI images FIGS. 8A, 8B, 8C (with diffusion sensitizing gradients applied along the left-right, anterior-posterior, and superior-inferior directions respectively) obtained with 8-shot EPI. Significantly aliasing artifacts are visible in uncorrected DWI data. The bottom row of FIG. 8 shows the magnitude summation of three raw DWI images (left, FIG. 8D), one of the embedded high-resolution navigator echoes (middle, FIG. 8E) acquired with parallel EPI with an acceleration factor of 4), and the MUSE reconstruction of 8-shot DWI data using the phase information derived from 4× parallel navigator echoes (right, FIG. 8F). It can be seen that the aliasing artifacts in uncorrected DWI can be effectively eliminated using s procedure that integrates the MUSE reconstruction algorithm and the interleaved DWI acquisition that includes parallel EPI based navigator echoes.

Figure 11A:
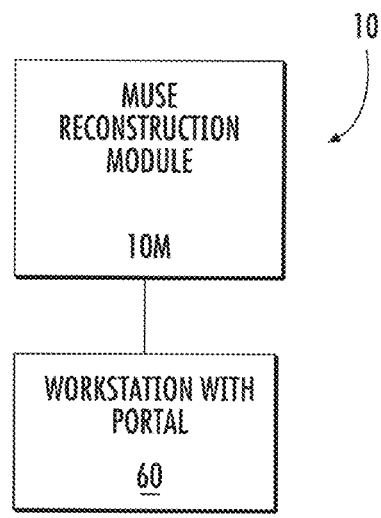
FIGS. 11A-11C are schematic illustrations of different systems that include or communicate with image processing circuits configured to carry out improved reconstruction to reduce artifact errors according to embodiments of the present invention.
Figure 11B:
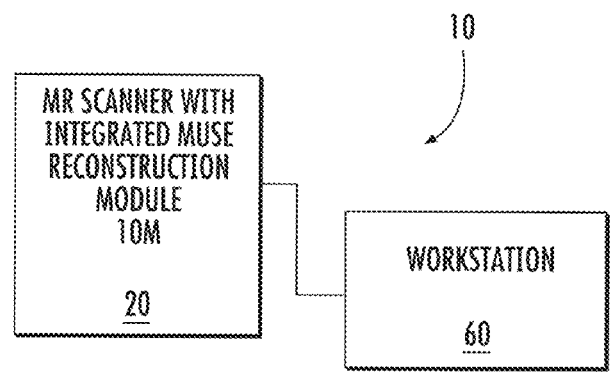
Figure 11C:
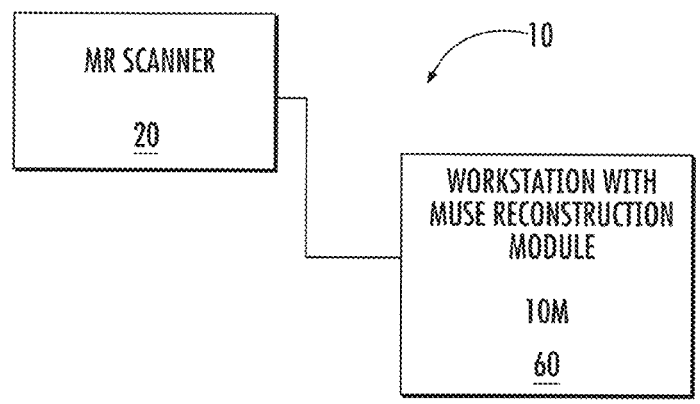

FIGS. 11A-11C illustrate exemplary image processing systems 10 with a MUSE reconstruction module or circuit 10M.

FIG. 11A illustrates that the system 10 can include at least one workstation 60 that has a portal for accessing the module 10M. The module 10M can be held on a remote server accessible via a LAN, WAN or Internet. The workstation 60 can communicate with patient image data which may be held in a remote or local server, in the Scanner or other electronically accessible database or repository. The workstation 60 can include a display with a GUI (graphic user input) and the access portal. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 11B illustrates that the module 10M can be included in the MR Scanner 20 which can communicate with a workstation 60. The module 10M can be integrated into the control cabinet with image processing circuitry.

FIG. 11C illustrates that the module 10M can be integrated into one or more local or remote workstations 60 that communicates with the Scanner 20. Although not shown, parts of the module 10M can be held on both the Scanner 20 and one or more workstations 60, which can be remote or local.

Some or all of the module 10M can be held on at least one server that can communicate with one or more Scanners 20. The at least one server can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Firewalls and suitable security protocols can be followed to exchange and/or analyze patient data.

Figure 12:
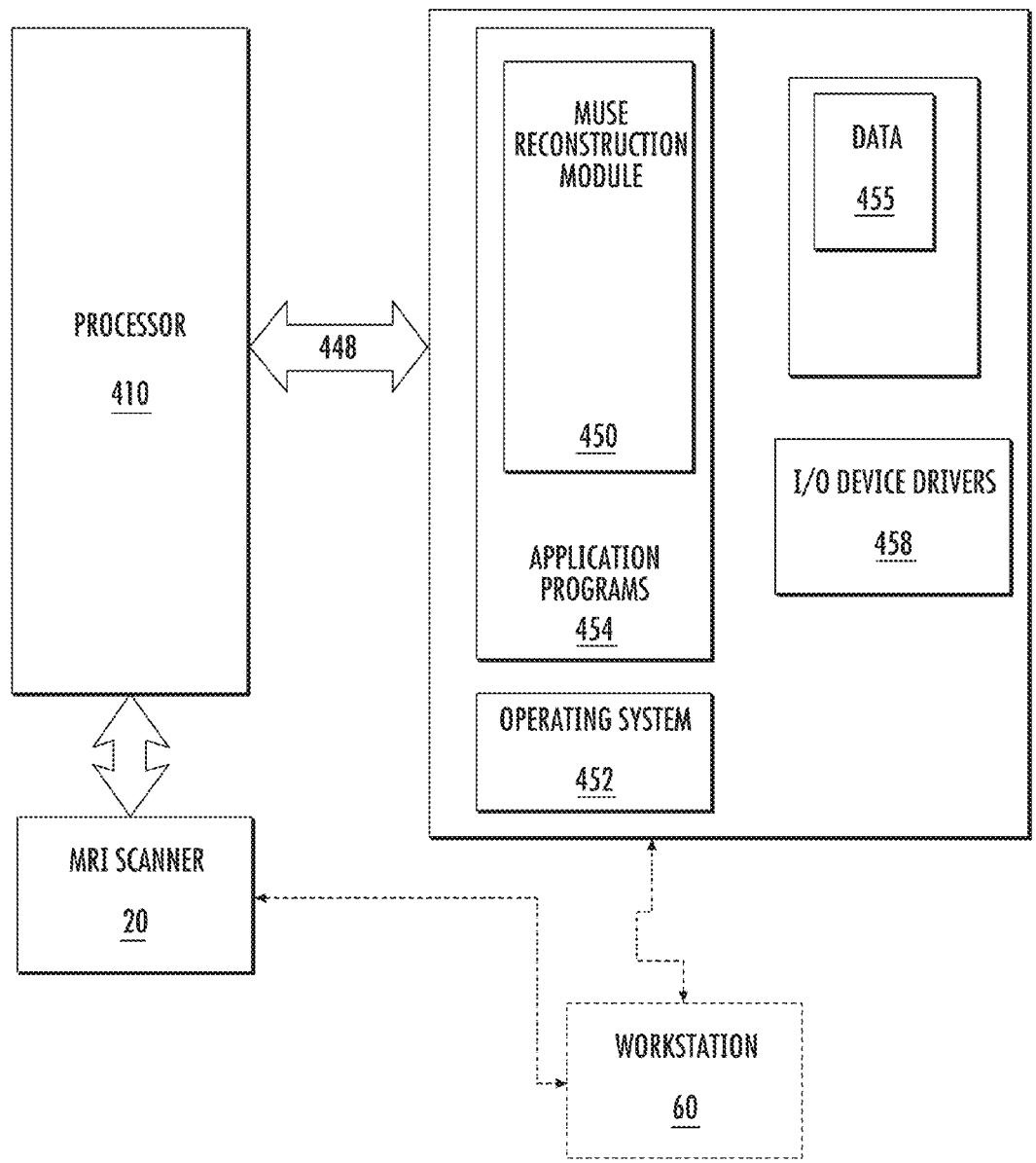
FIG. 12 is a schematic illustration of a data processing system according to embodiments of the present invention.

FIG. 12 is a schematic illustration of a circuit or data processing system 290. The system 290 can be used with any of the systems 10 and provide all or part of the module 10M. The circuits and/or data processing systems 290 data processing systems may be incorporated in a digital signal processor in any suitable device or devices. As shown in FIG. 12, the processor 410 can communicate with an MRI scanner 20 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 12 illustrates that the memory 414 may include several categories of software and data used in the data processing system: the operating system 452; the application programs 454; the input/output (I/O) device drivers 458; and data 455. The data 455 can include patient-specific MRI image data optionally including interleaved baseline T2-weighted EIP data and interleaved diffusion-weighted EPI data.

FIG. 12 also illustrates the application programs 454 can include a MUSE image reconstruction Module 450 that can correct for aliasing artifacts. The data processing system may be particularly suitable for DWI/DTI imaging of the brain but may be used for non-DWI imaging as well (e.g., fMRI). It is contemplated that the corrected image data can be used for more accurate cortical neuronal activity images and/or white matter evaluation including FA (fractional anisotropy) images and/or fiber tractography images.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Module 450 being an application program in FIG. 12, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 12 which is intended to encompass any configuration capable of carrying out the operations described herein. Further, Module 450 can communicate with or be incorporated totally or partially in other components, such as an MRI scanner 20, interface/gateway or workstation 60.

The I/O data port can be used to transfer information between the data processing system, the workstation, the MRI scanner, the interface/gateway and another computer system or a network (e.g., the Internet) or to other devices or circuits controlled by the processor. These components may be conventional components such as those used in many conventional data processing systems, which may be configured in accordance with the present invention to operate as described herein.

In conclusion, novel and robust techniques are described that allow high-resolution DWI through a multi-shot acquisition scheme, all inherently without the need for navigator and reference echoes. The MUSE technique can be readily incorporated with previous advances such as massive parallel imaging to further improve the spatial resolution for DWI and may find broad applications in modern neuroscience investigations of detailed brain microstructures and related functions where very high spatial resolution is required.

REFERENCES

[1] Le Bihan, Breton, Lallemand, Aubin, Vignaud, and Laval-Jeantet] Le Bihan, D., Breton, E., Lallemand, D., Aubin, M. L., Vignaud, J., Laval-Jeantet, M., 1988. Separation of diffusion and perfusion in intravoxel incoherent motion MR imaging. Radiology 168 (2), 497-505.

[2] Moseley, M. E., Cohen, Y., Kucharczyk, J., Mintorovitch, J., Asgari, H. S., Wendland, M. F., Tsuruda, J., Norman, D., August 1990. Diffusion-weighted mr imaging of anisotropic water diffusion in cat central nervous system. Radiology 176 (2), 439-45.

[3] Basser, P. J., Mattiello, J., LeBihan, D., 1994. MR diffusion tensor spectroscopy and imaging. Biophys J 66 (1), 259-67.

[4] Turner, R., Le Bihan, D., Chesnick, A. S., June 1991. Echo-planar imaging of diffusion and perfusion. Magn Reson Med 19 (2), 247-53.

[5] Anderson, A. W., Gore, J. C., September 1994. Analysis and correction of motion artifacts in diffusion weighted imaging. Magn Reson Med 32 (3), 379-87.

[6] Farzaneh, F., Riederer, S. J., Pelc, N. J., April 1990. Analysis of t2 limitations and off-resonance effects on spatial resolution and artifacts in echo-planar imaging. Magn Reson Med 14 (1), 123-39.

[7] Jezzard, P., Barnett, A. S., Pierpaoli, C., May 1998. Characterization of and correction for eddy current artifacts in echo planar diffusion imaging. Magn Reson Med 39 (5), 801-12.

[8] Griswold, M. A., Jakob, P. M., Heidemann, R. M., Nittka, M., Jellus, V., Wang, J., Kiefer, B., Haase, A., June 2002. Generalized autocalibrating partially parallel acquisitions (grappa). Magn Reson Med 47 (6), 1202-10.

[9] Butts, K., de Crespigny, A., Pauly, J. M., Moseley, M., May 1996. Diffusion-weighted interleaved echo-planar imaging with a pair of orthogonal navigator echoes. Magn Reson Med 35 (5), 763-70.

[10] Bammer, R., Stollberger, R., Augustin, M., Simbrunner, J., Offenbacher, H., Kooijman, H., Ropele, S., Kapeller, P., Wach, P., Ebner, F., Fazekas, F., June 1999. Diffusion-weighted imaging with navigated interleaved echo-planar imaging and a conventional gradient system. Radiology 211 (3), 799-806.

[11] Atkinson, D., Porter, D. A., Hill, D. L., Calamante, F., Connelly, A., July 2000. Sampling and reconstruction effects due to motion in diffusion-weighted interleaved echo planar imaging. Magn Reson Med 44 (1), 101-9.

[12] Pipe, J. G., Farthing, V. G., Forbes, K. P., January 2002. Multishot diffusion-weighted fse using propeller mri. Magn Reson Med 47 (1), 42-52.

[13] Wang, F.-N., Huang, T.-Y., Lin, F.-H., Chuang, T.-C., Chen, N.-K., Chung, H.-W., Chen, C.-Y., Kwong, K. K., November 2005. Propeller epi: an mri technique suitable for diffusion tensor imaging at high field strength with reduced geometric distortions. Magn Reson Med 54 (5), 1232-40.

[14] Skare, S., Newbould, R. D., Clayton, D. B., Bammer, R., June 2006. Propeller epi in the other direction. Magn Reson Med 55 (6), 1298-307.

[15] Atkinson, D., Counsell, S., Hajnal, J. V., Batchelor, P. G., Hill, D. L. G., Larkman, D. J., November 2006. Nonlinear phase correction of navigated multi-coil diffusion images. Magn Reson Med 56 (5), 1135-9.

[16] Porter, D. A., Heidemann, R. M., August 2009. High resolution diffusion-weighted imaging using readout-segmented echo-planar imaging, parallel imaging and a two-dimensional navigator-based reacquisition. Magn Reson Med 62 (2), 468-75.

[17] Li, Z., Pipe, J. G., Lee, C.-Y., Debbins, J. P., Karis, J. P., Huo, D., August 2011. X-prop: a fast and robust diffusion-weighted propeller technique. Magn Reson Med 66 (2), 341-7.

[18] Jeong, H.-K., Gore, J. C., Anderson, A. W., May 2012. High-resolution human diffusion tensor imaging using 2-d navigated multishot sense epi at 7 t. Magn Reson Med (E-pub ahead of print).

[19] Robson, M. D., Anderson, A. W., Gore, J. C., July 1997. Diffusion-weighted multiple shot echo planar imaging of humans without navigation. Magn Reson Med 38 (1), 82-8.

[20] Miller, K. L., Pauly, J. M., August 2003. Nonlinear phase correction for navigated diffusion imaging. Magn Reson Med 50 (2), 343-53.

[21] Liu, C., Bammer, R., Kim, D.-H., Moseley, M. E., December 2004. Self-navigated interleaved spiral (snails): application to high-resolution diffusion tensor imaging. Magn Reson Med 52 (6), 1388-96.

[22] Frank, L. R., Jung, Y., Inati, S., Tyszka, J. M., Wong, E. C., January 2010. High efficiency, low distortion 3d diffusion tensor imaging with variable density spiral fast spin echoes (3d dw vds rare). Neuroimage 49 (2), 1510-23.

[23] Pruessmann, K. P., Weiger, M., Scheidegger, M. B., Boesiger, P., November 1999. SENSE: sensitivity encoding for fast mri. Magn Reson Med 42 (5), 952-62.

[24] Feinberg, D. A., Moeller, S., Smith, S. M., Auerbach, E., Ramanna, S., Gunther, M., Glasser, M. F., Miller, K. L., Ugurbil, K., Yacoub, E., 2010. Multiplexed echo planar imaging for sub-second whole brain fmri and fast diffusion imaging. PLoS One 5 (12), e15710.

[25] Holdsworth, S. J., Aksoy, M., Newbould, R. D., Yeom, K., Van, A. T., Ooi, M. B., Barnes, P. D., Bammer, R., Skare, S., October 2012. Diffusion tensor imaging (dti) with retrospective motion correction for large-scale pediatric imaging. J Magn Reson Imaging 36 (4), 961-71.

[26] Andersson, J. L. R., Skare, S., May 2002. A model-based method for retrospective correction of geometric distortions in diffusion-weighted epi. Neuroimage 16 (1), 177-99.

[27] Mohammadi, S., Möller, H. E., Kugel, H., Müller, D. K., Deppe, M., October 2010. Correcting eddy current and motion effects by affine whole-brain registrations: evaluation of three-dimensional distortions and comparison with slicewise correction. Magn Reson Med 64 (4), 1047-56.

[28] Bydder, M., Atkinson, D., Larkman, D. J., Hill, D. L. G., Hajnal, J. V., March 2003. Smash navigators. Magn Reson Med 49 (3), 493-500.

[29] Bammer, R., Aksoy, M., Liu, C., January 2007. Augmented generalized sense reconstruction to correct for rigid body motion. Magn Reson Med 57 (1), 90-102.

[30] Chen, N.-K., Avram, A. V., Song, A. W., October 2011. Two-dimensional phase cycled reconstruction for inherent correction of echo-planar imaging nyquist artifacts. Magn Reson Med 66 (4), 1057-66.

[31] Reese, T. G., Heid, O., Weisskoff, R. M., Wedeen, V. J., January 2003. Reduction of eddy-current-induced distortion in diffusion mri using a twice-refocused spin echo. Magn Reson Med 49 (1), 177-82.

[32] Rudin, L., Osher, S., Fatemi, E., November 1992. Nonlinear total variation based noise removal algorithms. Physica D 60 (1-4), 259-268.

Any patents or publications mentioned in this specification are indicative of the levels of those skilled in the art to which the invention pertains. These patents and publications are herein incorporated by reference to the same extent as if each individual publication was specifically and individually indicated to be incorporated by reference at the location noted by the citation referencing the document. In case of conflict, the present specification, including definitions, will control.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. An MRI image data signal post-processing method for generating high-resolution diffusion-weighted imaging (DWI) images from multi-shot interleaved MRI pulse sequences, without relying on external navigator echoes, comprising:

programmatically estimating motion induced phase variations and position changes of a patient or subject among multiple segments of acquired DWI image data using parallel image reconstruction by 1) performing parallel MRI reconstruction of k-space data from each segment of DWI, 2) producing a full-FOV image from each DWI segment, and 3) measuring inter-segment phase variation and position change from the produced DWI images;

programmatically incorporating (i) shot-to-shot phase and position variations from the estimated motion induced phase variations and position changes and (ii) defined coil sensitivity profile data into a mathematical model that can jointly calculate magnitude-value source density signals that overlap in acquired uncorrected interleaved DWI image data to generate corrected DWI image data; and Programmatically generating high-resolution DWI images based on the corrected DWI image data to thereby generate images free from aliasing artifacts, wherein the multi-shot interleaved MRI pulse sequences are associated with interleaved echo-planar imaging (EPI) which generates EPI segments as the multiple segments or interleaved fast spin-echo (FSE) imaging which generates FSE segments as the multiple segments,
wherein the estimating motion induced phase and position variations from the acquired data comprises:
i. reconstructing images corresponding to different EPI or FSE segments by applying the parallel reconstruction to each individual EPI or FSE segment as the each DWI segment;
ii. mathematically quantifying phase and position changes among multiple images generated by the reconstruction as the measured inter-segment phase variation and position change; then
iii. spatially smoothing a shot-to-shot phase variation map derived from the mathematic quantification to produce phase information of high signal-to-noise ratio.

2. The method of claim 1, wherein the estimating motion induced phase variations and position changes is carried out by using one segment of the multiple segments as a reference segment of phase and position and calculating differences in signals associated with phase and position between the reference segment and other segments of the acquired DWI image data.

3. The method of claim 1, further comprising deriving coil sensitivity profile data for the parallel image reconstruction from a baseline T2-weighted EPI of a respective acquired DWI image data set.

4. The method of claim 1, wherein the phase variations between different EPI or FSE segments are calculated by comparing phase values of complex-value images corresponding to different segments.

5. The method of claim 1, wherein rotational and translational motions between different EPI or FSE segments are computed from k-space data corresponding to different segments.

6. The method of claim 1, wherein the spatial smoothing comprises a total variation algorithm that preserves sharp edge information of the phase variation map.

7. The method of claim 1, wherein DWI signals of the acquired image data from overlapping voxels are calculated by jointly performing parallel image reconstruction of all EPI or FSE segments for the reconstruction, with matrix inversion simultaneously applied to all EPI or FSE segments, assuming that magnitude-value signals are consistent across multiple segments in absence of large-scale intra-scan motion across segments.

8. The method of claim 1, wherein magnitude-value signals are considered consistent across multiple EPI or FSE segments, even in the presence of large-scale intrascan motion across segments, using a transformation matrix that reflects rotational and translational motion that is mathematically incorporated into a joint parallel image reconstruction from all EPI or FSE segments for the reconstruction.

9. The method of claim 1, wherein the high resolution DWI images are brain images illustrating brain structures based on properties of proton diffusivity.

10. The method of claim 1, further comprising generating fractional anisotropy (FA) maps of the brain using the high resolution DWI images.

11. A method for generating high-resolution diffusion-weighted imaging (DWI) and diffusion tensor imaging (DTI) images from multi-shot interleaved MRI pulse sequences that include external navigator echoes, comprising:
programmatically estimating motion induced phase variations and position changes of a subject or patient among multiple EPI or FSE segments from navigator echoes embedded in the interleaved MRI pulse sequences using parallel MRI image reconstruction by 1) performing parallel MRI reconstruction of k-space data from each EPI or FSE segment, 2) producing a full-FOV image from each segment, and 3) measuring inter-segment phase variation and position change from the produced images;
programmatically incorporating i) shot-to-shot phase and position variations and ii) known coil sensitivity data into a mathematical model that jointly calculates proton source density magnitude signals that overlap in uncorrected interleaved DWI data to generate corrected DWI data; and
generating high-resolution DWI and DTI images based on the corrected DWI data to thereby generate images free from aliasing artifacts,
wherein the estimating motion induced phase and position variations further comprises:
i. reconstructing images corresponding to different EPI or FSE segments by applying the parallel reconstruction to each individual EPI or FSE segment; and
ii. mathematically quantifying phase and position changes among multiple images generated by the reconstruction for the measurement of the inter-segment phase variation and position change; then
iii. spatially smoothing a shot-to-shot phase variation map derived from the mathematic quantification to produce phase information of high signal-to-noise ratio.

12. The method of claim 11, wherein the navigator echoes are acquired using either low resolution single-shot sequences or high resolution parallel single-shot sequences.

13. The method of claim 12, wherein the low resolution single-shot sequences comprise single-shot echo planar imaging (EPI) sequences.

14. The method of claim 12, wherein the high resolution parallel single-shot sequences comprises parallel single-shot EPI with an acceleration factor of 2 or 4.

15. The method of claim 11, further comprising deriving coil sensitivity profile data for the parallel image reconstruction from a baseline T2-weighted EPI of a respective acquired DWI image data set.

16. The method of claim 11, wherein the phase variations between different EPI or FSE segments are calculated by comparing phase values of complex-value images corresponding to different segments.

17. The method of claim 11, wherein the spatial smoothing comprises a total variation algorithm that preserves sharp edge information of the phase variation map or any other spatial smoothing procedure.

18. The method of claim 11, wherein DWI signals from overlapping voxels of the image data are calculated by jointly performing parallel image reconstruction of all EPI or FSE segments for the reconstruction, with matrix inversion applied simultaneously to all EPI or FSE segments, assuming that magnitude-value signals are consistent across multiple segments in absence of large-scale intra-scan motion across segments, and wherein phase variations across multiple EPI or FSE segments are calculated based on the estimated phase variations and position changes.

19. The method of claim 1, wherein magnitude-value signals are considered consistent across multiple EPI or FSE segments, even with large-scale intrascan motion across segments, using a transformation matrix that reflects rotational and translational motion that is mathematically incorporated into a joint parallel image reconstruction from all EPI or FSE segments for the (i) reconstruction.

20. A method for generating high-resolution fMRI images or other types of non-diffusion weighted imaging (DWI) images from multi-shot interleaved MRI pulse sequences, without relying on external navigator echoes, comprising:

programmatically estimating motion induced phase variations and position changes of a patient or subject among multiple echo planar imaging (EPI) or spiral segments from acquired image data using parallel image by 1) performing parallel MRI reconstruction of k-space data from each segment, 2) producing a full-FOV image from each segment, and 3) measuring inter-segment phase variation and position change from the produced images;

programmatically incorporating i) shot-to-shot phase and position variations from the estimated motion induced phase variations and position changes and ii) calculated or known coil sensitivity data into a mathematical model that jointly calculates proton source density signals that overlap in uncorrected interleaved fMRI data or non-DWI data to generate corrected interleaved image data; and generating high-resolution fMRI images or other non-DWI images using the corrected interleaved image data to thereby generate images without aliasing artifacts, wherein the estimating motion induced phase and position variations from the acquired data further comprises:

i. reconstructing images corresponding to different EPI or spiral segments by applying the parallel reconstruction to each individual EPI or spiral segment; and ii. mathematically quantifying phase and position changes among multiple images generated by the reconstruction; then iii. spatially smoothing a shot-to-shot phase variation map derived from the mathematic quantification to produce phase information of high signal-to-noise ratio.

21. A method for generating high-resolution fMRI images or other types of images using non-diffusion weighted imaging (DWI) data from multi-shot interleaved MRI pulse sequences that include external navigator echoes, comprising:

programmatically estimating motion induced phase variations and position changes of a subject or patient among multiple echo planar imaging (EPI) or spiral segments from navigator echoes embedded in the interleaved MRI pulse sequences by 1) performing parallel MRI reconstruction of k-space data from each segment, 2) producing a full-FOV image from each segment, and 3) measuring inter-segment phase variation and position change from the produced images;

incorporating i) shot-to-shot phase and position variations derived from the programmatic estimations and ii) calculated or known coil sensitivity data into a mathematical model that jointly calculates proton source density signals that overlap in the uncorrected interleaved fMRI or other types of non-DWI image data to generate corrected image data; and generating high-resolution fMRI images or other non-DWI images using the corrected image data, wherein the estimating motion induced phase and position variations from the acquired data further comprises:

i. reconstructing images corresponding to different EPI or spiral segments by applying the parallel reconstruction to each individual EPI or spiral segment; and ii. mathematically quantifying phase and position changes among multiple images generated by the reconstruction; then iii. spatially smoothing a shot-to-shot phase variation map derived from the mathematic quantification to produce phase information of high signal-to-noise ratio.

22. An image processing circuit that is at least one of onboard or in communication with an MRI system configured to electronically carry out the method of claim 1.

23. An MR image processing system that is at least one of onboard or in communication with an MRI system comprising at least one processor configured to carry out the method of claim 1.

24. A data processing system comprising non-transitory computer readable storage medium having computer readable program code embodied in the medium, the computer-readable program code comprising computer readable program code configured to carry out the method of claim 1, wherein the data processing system is at least one of onboard or in communication with an MRI system.

25. An image processing circuit that is at least one of onboard or in communication with an MRI system configured to electronically carry out the method of claim 11.

26. An MRI image processing system that is at least one of onboard or in communication with an MRI system comprising at least one processor configured to carry out the method of claim 11.

27. A data processing system comprising non-transitory tangible computer readable storage medium having computer readable program code embodied in the medium, the computer-readable program code comprising computer readable program code configured to carry out the method of claim 11, wherein the data processing system is at least one of onboard or in communication with an MRI system.

28. The method of claim 1, wherein the mathematical model comprises a transformation matrix using the estimated phase variation and position changes which can include rotational and translational motion of >1 voxel.

29. The method of claim 1, further comprising unfolding overlapping voxels in all image-domain columns of a transformation matrix simultaneously to programmatically generate high resolution DWI images free from aliasing artifact.

30. The method of claim 20, wherein the multi-shot interleaved MRI pulse sequences are associated with interleaved echo-planar imaging (EPI) which generates the EPI segments as the multiple segments or interleaved spiral imaging which generates the spiral segments as the multiple segments.

31. The method of claim 20, wherein the phase variations between different EPI or spiral segments are calculated by comparing phase values of complex-value images corresponding to different segments.

32. The method of claim 20, wherein rotational and translational motions between different EPI or spiral segments are computed from k-space data corresponding to different segments.

33. The method of claim 20, wherein the phase information is spatially smoothed using a spatial smoothing protocol that preserves sharp edge information of a phase variation map.

34. The method of claim 20, wherein the images are fMRI images comprising fMRI signals from overlapping voxels which are calculated by jointly performing parallel image reconstruction of all EPI or spiral segments for the reconstruction, with matrix inversion simultaneously applied to all EPI or spiral segments, assuming that magnitude-value signals are consistent across multiple segments in absence of large-scale intra-scan motion across segments, and wherein phase variations across multiple EPI or spiral segments are calculated based on the estimated phase variations and position changes.

35. The method of claim 20, wherein magnitude-value signals are considered consistent across multiple EPI or spiral segments, even with large-scale intrascan motion across segments, using a transformation matrix that reflects rotational and translational motion that is mathematically incorporated into a joint parallel image reconstruction from all EPI or spiral segments for the reconstruction.

36. The method of claim 21, wherein the multi-shot interleaved MRI pulse sequences are associated with interleaved echo-planar imaging (EPI) which generates the EPI segments as the multiple segments or interleaved spiral imaging which generates the spiral segments as the multiple segments.

37. The method of claim 21, wherein the phase variations between different segments for the measurements are calculated by comparing phase values of complex-value images corresponding to different segments.

38. The method of claim 21, wherein rotational and translational motions between different segments for the measurements are computed from k-space data corresponding to different segments.

39. The method of claim 21, wherein phase information is spatially smoothed using a spatial smoothing protocol that preserves sharp edge information of the phase variation map.

40. The method of claim 39, wherein the spatial smoothing protocol comprises a total variation algorithm.

41. The method of claim 21, wherein image data signals from overlapping voxels are calculated by jointly performing parallel image reconstruction of all segments for the reconstruction, with matrix inversion simultaneously applied to all segments, assuming that magnitude-value signals are consistent across multiple segments in the absence of large-scale intra-scan motion across segments, and wherein phase variations across multiple segments are calculated based on the estimated phase variations and position changes.

42. The method of claim 21, wherein magnitude-value signals are considered consistent across multiple segments, even in the presence of large-scale intrascan motion across segments, using a transformation matrix that reflects rotational and translational motion that is mathematically incorporated into a joint parallel image reconstruction from all segments for the reconstruction.

* * * * *

UNITED STATES PATENT AND TRADEMARK OFFICE
CERTIFICATE OF CORRECTION

PATENT NO. : 9,886,745 B2  
APPLICATION NO. : 14/409355  
DATED : February 6, 2018  
INVENTOR(S) : Chen et al.

Page 1 of 1

It is certified that error appears in the above-identified patent and that said Letters Patent is hereby corrected as shown below:

In the Specification

Column 14, Line 46: Please correct "$e^{i\varphi p}$" to read -- $e^{i\varphi}$ --

Column 14, Line 64: Please correct "(c,y)" to read -- (x,y) --

Signed and Sealed this  
Fifth Day of June, 2018

Andrei Iancu  
*Director of the United States Patent and Trademark Office*